(12) United States Patent
Atkins et al.

(10) Patent No.: US 10,889,500 B2
(45) Date of Patent: Jan. 12, 2021

(54) METHODS FOR PRODUCING GRAPHENE FROM COAL

(71) Applicant: CARBON HOLDINGS INTELLECTUAL PROPERTIES, LLC, Sheridan, WY (US)

(72) Inventors: Charles Agee Atkins, Sheridan, WY (US); Garrett W. Lindemann, Buffalo, WY (US); Matthew Targett, Bainbridge Island, WA (US)

(73) Assignee: Carbon Holdings Intellectual Properties, LLC, Sheridan, WY (US)

( * ) Notice: Subject to any disclaimer, the term of this patent is extended or adjusted under 35 U.S.C. 154(b) by 0 days.

(21) Appl. No.: 16/230,318

(22) Filed: Dec. 21, 2018

(65) Prior Publication Data
US 2019/0194022 A1 Jun. 27, 2019

Related U.S. Application Data

(60) Provisional application No. 62/610,037, filed on Dec. 22, 2017.

(51) Int. Cl.
*C01B 32/336* (2017.01)
*C01B 32/184* (2017.01)
(Continued)

(52) U.S. Cl.
CPC .............. *C01B 32/336* (2017.08); *C01B 3/02* (2013.01); *C01B 32/05* (2017.08); *C01B 32/154* (2017.08); *C01B 32/158* (2017.08); *C01B 32/16* (2017.08); *C01B 32/182* (2017.08); *C01B 32/184* (2017.08); *C01B 32/20* (2017.08);
(Continued)

(58) Field of Classification Search
CPC ....... C01B 32/336; C01B 32/30; C01B 32/20; C01B 32/182; C01B 32/158; C01B 53/04; C01B 32/205; C01B 32/05; C01B 32/154; C01B 32/16; C01B 32/184; C01B 3/02; C01B 32/50; C08F 6/28; C08F 10/02; C08F 10/06; C08F 20/44; C10B 53/00; C10B 57/08; D01F 9/15; D01F 9/12; C10C 3/002; C10C 3/00; C10G 1/002; C10G 1/02;
(Continued)

(56) References Cited

U.S. PATENT DOCUMENTS 3,639,953 A  2/1972 Kimura et al.
4,439,304 A  3/1984 Sudbury et al.
(Continued)

FOREIGN PATENT DOCUMENTS

CN  105836739 A  * 8/2016

OTHER PUBLICATIONS

IUPAC. Compendium of Chemical Terminology, 2nd ed. (the "Gold Book"). Compiled by A. D. McNaught and A. Wilkinson. Blackwell Scientific Publications, Oxford (1997). Online version (2019-) created by S. J. Chalk. ISBN 0-9678550-9-8. https://doi.org/10.1351/goldbook.*

(Continued)

*Primary Examiner* — Richard M Rump
(74) *Attorney, Agent, or Firm* — Dorsey & Whitney LLP

(57) ABSTRACT

A method of preparing graphene from coal can include thermally processing raw coal and, after the coal has been at least partially cooled from thermal processing, forming reduced graphene oxide from the coal.

12 Claims, 11 Drawing Sheets

(51) Int. Cl.

| | |
|---|---|
| *C01B 3/02* | (2006.01) |
| *G01N 33/22* | (2006.01) |
| *C10C 3/00* | (2006.01) |
| *D01F 9/12* | (2006.01) |
| *C01B 32/50* | (2017.01) |
| *C01B 32/30* | (2017.01) |
| *C01B 32/20* | (2017.01) |
| *C01B 32/182* | (2017.01) |
| *C01B 32/158* | (2017.01) |
| *C10B 53/04* | (2006.01) |
| *C01B 32/205* | (2017.01) |
| *C01B 32/05* | (2017.01) |
| *C01B 32/154* | (2017.01) |
| *C01B 32/16* | (2017.01) |
| *C08F 6/28* | (2006.01) |
| *C10B 53/00* | (2006.01) |
| *C10B 57/08* | (2006.01) |
| *D01F 9/15* | (2006.01) |
| *C08F 10/02* | (2006.01) |
| *C08F 10/06* | (2006.01) |
| *C08F 20/44* | (2006.01) |
| *C10G 1/00* | (2006.01) |
| *C10G 1/02* | (2006.01) |
| *C10G 1/04* | (2006.01) |
| *C10G 17/02* | (2006.01) |
| *C10G 27/12* | (2006.01) |

(52) U.S. Cl.
CPC ............ *C01B 32/205* (2017.08); *C01B 32/30* (2017.08); *C01B 32/50* (2017.08); *C08F 6/28* (2013.01); *C08F 10/02* (2013.01); *C08F 10/06* (2013.01); *C08F 20/44* (2013.01); *C10B 53/00* (2013.01); *C10B 53/04* (2013.01); *C10B 57/08* (2013.01); *C10C 3/00* (2013.01); *C10C 3/002* (2013.01); *C10G 1/002* (2013.01); *C10G 1/02* (2013.01); *C10G 1/04* (2013.01); *D01F 9/12* (2013.01); *D01F 9/15* (2013.01); *G01N 33/222* (2013.01); *C10G 17/02* (2013.01); *C10G 27/12* (2013.01); *D10B 2101/12* (2013.01)

(58) Field of Classification Search
CPC .......... C10G 1/04; C10G 17/02; C10G 27/12; G01N 33/222; D10B 2101/12
See application file for complete search history.

(56) References Cited

U.S. PATENT DOCUMENTS

| | | | |
|---|---|---|---|
| 4,804,390 A | 2/1989 | Lloyd et al. | |
| 5,692,807 A | 12/1997 | Zimmerman | |
| 8,148,435 B2 | 4/2012 | Fiato | |
| 9,074,138 B2 | 7/2015 | Rinker | |
| 2009/0061193 A1 | 3/2009 | Hara et al. | |
| 2011/0011719 A1 | 1/2011 | Rinker | |
| 2012/0076703 A1 | 3/2012 | Stiller et al. | |
| 2014/0120030 A1* | 5/2014 | Kim | B82Y 30/00 423/448 |
| 2014/0223882 A1 | 8/2014 | Shah et al. | |
| 2016/0060122 A1* | 3/2016 | Tour | C01B 32/192 423/415.1 |
| 2017/0198221 A1 | 7/2017 | Targett et al. | |
| 2018/0155201 A1 | 6/2018 | Zhang | |

OTHER PUBLICATIONS

Ye, Ruquan, et al. "Bandgap engineering of coal-derived graphene quantum dots. (Supporting Information)" ACS applied materials & interfaces 7.12 (2015): S1-S5.*
Andrésen, John M., et al. "Synthesis of pitch materials from hydrogenation of anthracite." Fuel processing technology 85.12 (2004): 1361-1372.*
Li, Gang, et al. "One-step green synthesis of nitrogen and phosphorus co-doped pitch-based porous graphene-like carbon for supercapacitors." Journal of Porous Materials 24.6 (2017): 1689-1696.*
International Search Report and Written Opinion for PCT Application No. PCT/US2018/067351, dated May 2, 2019.
International Search Report and Written Opinion for PCT Application No. PCT/US2018/067341, dated May 23, 2019.
Kim, et al., "Pitch-Based Carbon Fibers From Coal Tar or Petroleum Residue Under the Same Processing Condition", Carbon Letters vol. 19, Jun. 14, 2016, 72-78.

* cited by examiner

METHODS FOR PRODUCING GRAPHENE FROM COAL

CROSS-REFERENCE TO RELATED APPLICATIONS

The present application claims the benefit of U.S. Provisional Patent Application No. 62/610,037 filed on 22 Dec. 2017, titled "Methods for Producing Advanced Carbon Materials from Coal," the disclosure of which is incorporated herein, by reference, in its entirety.

BACKGROUND

Coal is a highly varied heterogeneous material that has been mined and principally used for three purposes over thousands of years: 1) the generation of thermal heat and power generation through incineration, 2) the production of steel and other metals by coking, and 3) the production of what are now widely known as "petrochemicals" through pyrolysis or liquefaction. Despite the fact that coal has been extensively used for thousands of years, more than 99% of it has been incinerated to produce heat and power. This process is now widely known to produce a host of adverse environmental and economic effects.

Additional uses of coal has been the topic of research for many years. The basic chemistry of coal was well understood by at least the early twentieth century. Significant research was conducted with the aim of deriving liquid transportation fuels from coal in order to supplant petroleum. One notable breakthrough was the development of the Fischer-Tropsch process in Germany, around 1925, which converted gasified coal into liquid hydrocarbons. Additionally, Sasol, a major South African company, focused on the conversion of solid coal to liquid transportation fuels via catalytic cracking. Similarly, the United States Department of Energy sought to develop coal-based transportation fuels as an alternative to petroleum-based fuels. However, due to research driven petroleum technology and the decreasing costs of petroleum, the use of coal to produce liquid transportation fuels at large scales never became economically feasible.

Although significant research has been conducted on coal liquefaction and the use of coal to form other products for more than a century, the ability to produce high-value, high-performance carbon based products from coal remains an open question. In recent years, carbon-based technologies have come to the forefront, with rapid developments being made in the commercialization of advanced carbon materials such as carbon fiber, graphene, and carbon nanotubes. As these advanced materials are increasingly used in mass produced, high volume applications, there is a need to quickly and economically supply large quantities of advanced carbon materials to manufacturers. Thus, while improvements in the derivation of fuels and other products from coal are being explored, there remains significant work to be done in developing processes to convert coal into the advanced carbon materials that will be instrumental in the economy of the future.

SUMMARY

A method of producing graphene from coal includes thermally processing coal at a temperature of at least about 300° F., and after the coal has been at least partially cooled from thermal processing, forming reduced graphene oxide from the coal.

In some cases, forming reduced graphene oxide from the coal can include oxidizing the coal to form a coal oxide, centrifuging the coal oxide, collecting precipitate from the coal oxide after centrifuging, the precipitate comprising graphene oxide, and reducing the graphene oxide to form reduced graphene oxide. Oxidizing the coal to form a coal oxide includes mixing the coal with at least one of sulfuric acid, nitric acid, or potassium permanganate, or hydrogen peroxide to form the coal oxide. Mixing the coal with at least one of sulfuric acid, nitric acid, potassium permanganate, or hydrogen peroxide to form the coal oxide can include mixing the coal with at least one of sulfuric acid and nitric acid, stirring the coal mixed with at least one of the sulfuric acid and the nitric acid, mixing potassium permanganate to the coal mixed with at least one of the sulfuric acid and the nitric acid, stirring the coal mixed with the potassium permanganate and at least one of the sulfuric acid and the nitric acid, diluting, with water, the coal mixed with the potassium permanganate and at least one of the sulfuric acid and the nitric acid to form a solution, mixing the solution with hydrogen peroxide, performing a first centrifugation of the solution mixed with the hydrogen peroxide, after performing the first centrifugation, separating a supernatant of the solution mixed with the hydrogen peroxide from precipitate of the solution mixed with the hydrogen peroxide, the supernatant including the coal oxide.

The method can further include diluting, with water, the coal oxide before centrifuging the coal oxide. In some cases, reducing the graphene oxide to form reduced graphene oxide includes sonicating the graphene oxide, and hydrothermally treating the graphene oxide in a par reactor after sonicating the graphene oxide. In some cases, thermally processing coal at a temperature of at least about 300° F. includes heating the coal to a first temperature not to exceed 350° F., transferring the coal to a mercury removal reactor, heating the coal in the mercury removal reactor to a second temperature of at least 500° F., and contacting the coal with an inert gas to remove at least a portion of mercury present in the coal. In some cases, forming reduced graphene oxide from the coal includes forming the reduced graphene oxide from the coal at a reduced graphene oxide yield rate of between approximately 10 weight percent and approximately 20 weight percent of the coal. In some cases, forming reduced graphene oxide from the coal includes retaining a predetermined amount of one or more impurity atoms present in the amount of coal in the reduced graphene oxide. In some cases, the impurity atoms include one or more of boron, nitrogen, and silicon.

A method of producing synthetic graphene can include beneficiating an amount of coal including one or more impurity atoms to remove a predetermined amount of the one or more impurity atoms therefrom, processing the beneficiated amount of coal to produce an amount of pitch from at least some of the amount of coal, and treating at least some of the amount of pitch to produce the synthetic graphene, wherein the synthetic graphene includes a desired amount of the one or more impurity atoms. In some cases, the amount of pitch includes mesophase pitch. In some cases, the impurity atoms include one or more of silicon, nitrogen, and boron. In some cases, the impurity atoms result in a predetermined amount of point defects in the synthetic graphene.

A method of producing synthetic graphene can include thermally processing an amount of coal to achieve a predetermined concentration of one or more impurity atoms in the amount of coal, oxidizing at least some of the amount of coal to form a coal oxide including a predetermined concentration of one or more impurity atoms, and processing the coal oxide to form reduced graphene oxide including a predetermined concentration of one or more impurity atoms.

In some cases, the one or more impurity atoms occur naturally in the amount of coal. In some cases, the impurity atoms include one or more of cadmium, selenium, boron, nitrogen, and silicon. In some cases, the predetermined concentration of the impurity atoms in the reduced graphene oxide is from about 0.1 atomic % to about 10 atomic %.

A synthetic graphene formed from an amount coal can include a predetermined amount of dopant atoms, the dopant atoms derived from the amount of coal. In some cases, the dopant atoms include one or more of boron, nitrogen, and silicon. The synthetic graphene can further include a predetermined amount of point defects due to the one or more dopant atoms.

BRIEF DESCRIPTION OF THE DRAWINGS

The accompanying drawings illustrate various embodiments of the present apparatus and are a part of the specification. The illustrated embodiments are merely examples of the present apparatus and do not limit the scope thereof.

Throughout the drawings, identical reference numbers designate similar, but not necessarily identical, elements.

DETAILED DESCRIPTION

Figure 1:
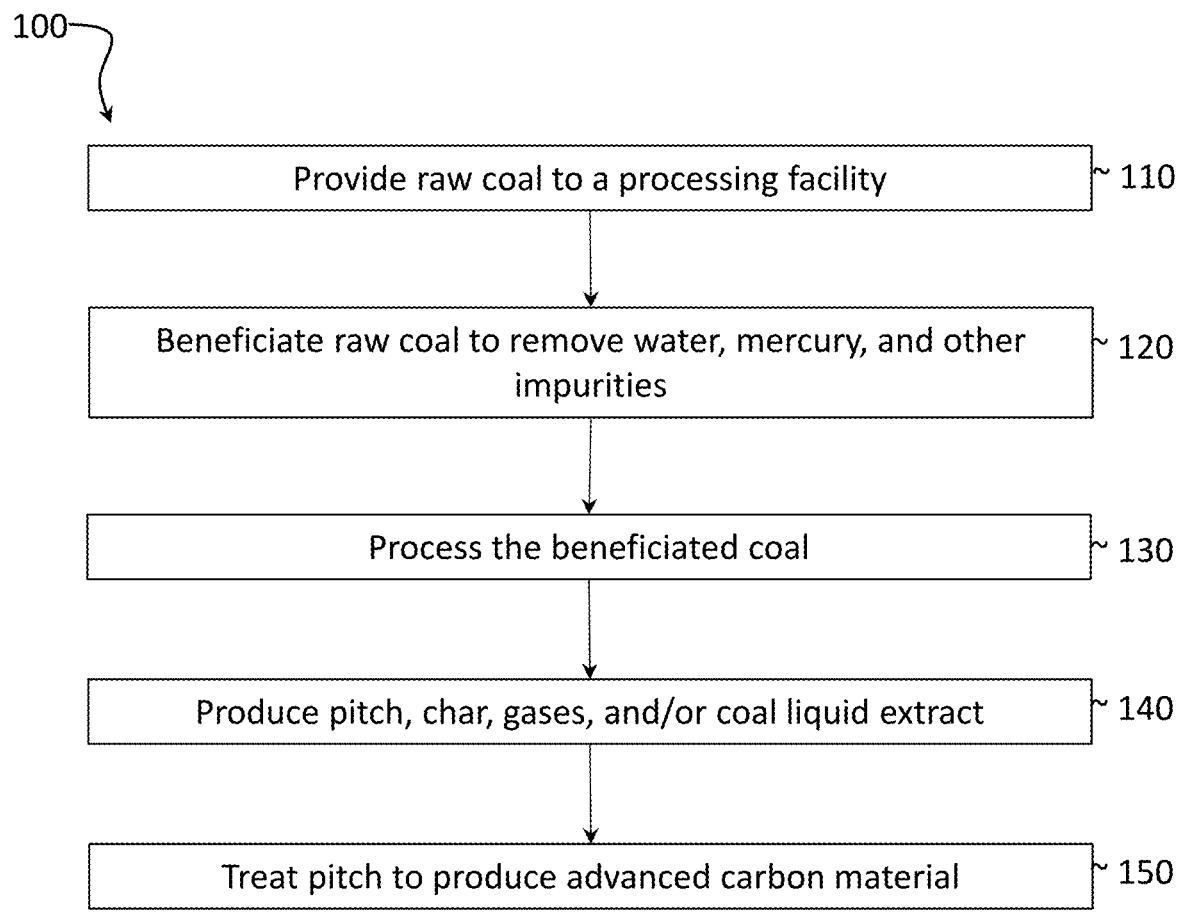
FIG. 1 illustrates a process flow diagram of an example of a method of producing advanced carbon materials from coal in accordance with the present disclosure.

As described below, advanced carbon materials can be produced from raw, mined coal. In some embodiments, raw coal can be transported to a processing facility which can then produce graphene or other advanced carbon materials therefrom. The coal can then be beneficiated in order to remove a desired amount of impurities, for example mercury, arsenic, cadmium, other heavy metals, water, and volatile compounds. In some cases, beneficiation can include heating the coal to remove these impurities. The beneficiated coal can then be processed to produce a pitch, activated carbon, and/or other precursors or advanced carbon materials. The processing can include subjecting the beneficiated coal to a pyrolysis process, direct liquefaction process, indirect liquefaction process, or processing involving one or more membranes. In some cases, these processes can produce byproducts, such as gases, solid char, and coal liquid extract which themselves can be processed to form useful materials, such as other advanced carbon materials. For example, solid char can be processed to form activated carbon, and coal liquid extracted can be processed to form aromatic compounds such as benzene and paraxylene.

In some embodiments, the pitch produced by the processes described herein can be an isotropic pitch, and can be converted to a mesophase pitch by processing as needed or desired. The pitch can then be treated to produce one or more advanced carbon materials. In some cases, the pitch can be processes to form synthetic graphite, which can be subjected to further processing to form or produce synthetic graphene having one or more desired physical, chemical, and/or electrical properties. In some cases the pitch can be spun to form carbon fibers. These advanced carbon materials can be subjected to further processing, or can be delivered to third parties for use, for example in manufacturing. In some cases one or more advanced carbon materials can be produced and combined to form secondary material, such as a carbon reinforced polymer.

In some embodiments, one or more gases can be generated or produced during beneficiation, pitch production, and/or other coal processing steps as described herein. In some cases, these gases can be captured or otherwise contained and/or used during the processes described herein. The gases captured during certain process steps can be used in subsequent process steps, for example in the production or refinement of advanced carbon materials as described herein. In some cases, gases produced by and a captured as part of the processes described herein can be utilized by these same or subsequent processes in order to increase the efficiency and/or cost effectiveness of said processes. In some cases, these gases can be used as in the formation of advanced carbon materials as described herein, for example as precursors to advanced carbon materials. Thus, in some cases, gases produced by coal as described herein can be used to form advanced carbon materials. In some embodiments, the captured gas or gases can comprise hydrogen and/or carbon. In some cases, the captured gas or gases can comprise sulfur. Such gases can include, for example, $H_2$, $CO_2$, $CO$, $CH_4$, $C_2H_4$, $C_3H_6$, and/or other hydrocarbon gases.

In some embodiments, one or more of the processes or process steps described herein can utilize or be carried out in the presence of one or more catalysts. For example, one or more process can include a hydrogenation catalyst. In some embodiments, the catalyst can comprise a metal, for example platinum. In some cases, the catalyst can be a multi-part catalyst, for example a catalyst comprising two or more metals. In some cases, a catalyst can include a ceramic or mineral material, for example a silicate material, such as an aluminosilicate material. In some cases, a catalyst can include any catalytic material now known or as can yet be discovered for use in processing coal.

In some embodiments, all of the beneficiation, processing, and treatment steps described herein can be performed at a single processing facility, for example a single processing plant or compound. However, in other embodiments, one or more steps can be performed at separate facilities and the products of each step can be stored and transported between each facility. As used herein, the term processing facility can refer to one or more laboratories, buildings, process flows, or other apparatuses at about the same geographic location. For example, a processing facility can comprise a single building or factory complex at a single geographic location which comprises such equipment to perform the processes and methods described herein.

The advanced carbon materials which can be produced by the processes described herein can include, but are not limited to, graphene, carbon fibers, carbon foams, single-walled carbon nanotubes, multi-walled carbon nanotubes, carbon megatubes, graphite, graphite nano-platelets, nanoribbons, nanobuds, fullerenes, such as buckminsterfullerene and multi-cored fullerenes, quantum dots, activated carbon, and pyrolyzed carbon. The advanced carbon materials produced by the processes described herein can also include, but are not limited to resins and polymers, such as polyacrylonitrile, polyurethane resins, cyanate ester resins, epoxy resins, methacrylate resins, polyester resins, and others. The advanced carbon materials produced by the processes described herein can also include materials that can be used as precursors in the formation of other advanced carbon materials. In some cases, these advanced carbon materials can include alkanes, alkenes, and/or alkynes. In some cases, advanced carbon materials can comprise biologically useful materials or biopolymers, such as proteins, amino acids, nucleic acids, collagen, chitosan, and/or sugars.

In some embodiments, coal can be provided by any method that is now known or that can be developed in the future. For example, coal is generally extracted from naturally occurring layers or veins, known as coal beds or coal seams, by mining. Coal can be extracted by surface mining, underground mining, or various other forms of mining. Typically, coal that has been extracted via mining, but has not been otherwise processed is referred to as raw coal. In some embodiments, raw coal can be provided to a processing facility and used to produce advanced carbon materials as described herein. In some cases, the raw coal can be extracted via a surface mining process, such as a high wall mining process, strip mining process, or contour mining process. In some cases, the raw coal can be extracted via an underground mining process, such as by a longwall mining process, continuous mining process, blast mining process, retreat mining process, or room and pillar mining process.

The raw coal can be mined or extracted from a location relatively near to the processing facility. For example, the processing facility can be located at, or near a coal extraction area. However, in other cases coal can be extracted from any location and transported to the processing facility. In some cases raw coal can be provided to the processing facility as needed to produce a desired amount of advanced carbon materials. However, in some other cases, raw coal can be provided and stored at the processing facility until it is processed.

Coal can be ranked or graded based on its contents and properties. Although a variety of coal classification schemes exist, a general metamorphic grade is used herein to generally describe raw coal. These grades are used generally to aid in the understanding of the present disclosure and are not intended to limit to types of coal which can be used to produce advanced carbon materials as described herein. While certain classifications of coal can be preferable for use in the processes described herein, such processes are not strictly limited to the discussed classifications of coal, if any. In some embodiments, the coal utilized by the processes described herein can be lignite coal, and can have a volatile content of greater than about 45 wt. %. In some embodiments, the coal can be sub-bituminous coal, bituminous coal, and/or anthracite coal. In some embodiments, the coal can be coal extracted from the Brook Mine near Sheridan, Wyo. In some cases, the preferred coal for use in the processes described herein can be selected by the skilled artisan. According to some embodiments, and as illustrated in FIG. 1, graphene or another advanced carbon material can be produced from coal by a method or process 100 including:

providing coal to a processing facility at block 110;

beneficiating the coal via the processing facility at block 120 to remove a desired amount of water, metals, and/or other impurities from the coal;

processing at least some of the beneficiated coal via the processing facility at block 130;

producing pitch, char, gases, and/or coal liquid extract at block 140; and treating the pitch via the processing facility at block 150 to produce the graphene or other advanced carbon material.

Although the method 100 describes a process flow for producing a single type of advanced carbon material via a processing facility, the method 100 can be used to produce more than one type of advanced carbon material via the processing facility. For example, the method 100 can be utilized to produce an amount of a first advanced carbon material and subsequently used to produce an amount of a second, different advanced carbon material. In some cases however, the processing facility can be able to produce two or more different types of advanced carbon materials via parallel processing utilizing the method 100. Further, while producing pitch, char, and/or coal liquid extract is described as a separate block 140, the pitch, char, and/or coal liquid extract can be produced as a result of blocks 120 and/or 130 and may not be a separate process step in and of itself.

As described herein, raw coal can be provided to a processing facility at block 110 for use in the method 100. The processing facility can have the capacity to store raw coal for use as needed, or can receive raw coal as needed to produce a desired amount of advanced carbon material. As is well known in the art, coal can be provided via truck, train, or any other form of transportation. Further, the processing facility can be situated at a coal extraction site, such that coal extraction site can be considered as part of the processing facility.

At block 120, the raw coal can be beneficiated to remove contaminants or impurities such as water, heavy metals, and/or volatile compounds from the raw coal, thereby producing beneficiated or upgraded coal. In some cases, the beneficiation process can comprise heating the raw coal to a desired temperature for a first duration. In some embodiments, beneficiation can also include heating the raw coal to a second, higher desired temperature of a second duration. In some embodiments, the coal can be heated in an atmosphere comprising a halogen gas. In some embodiments, beneficiation can include subjecting the raw coal to a WRITECoal beneficiation process, as described, for example, in U.S. Pat. No. 9,181,509 which is hereby incorporate by reference in its entirety. In some other embodiments, the coal can be beneficiated by heating the coal to a desired temperature in the presence of one or more catalyst compounds. In some cases, beneficiating the coal can comprise pyrolyzing the coal, for example in the presence of a catalyst. In some cases, the coal can be beneficiated by the BenePlus System, as developed and licensed by LP Amina and as described, for example, in U.S. Patent Publication No. 2017/0198221 which is hereby incorporated by reference in its entirety.

The beneficiated coal can comprise a significantly reduced amount of mercury, cadmium, other heavy metals, water, and/or other impurities. As used herein, an impurity can be considered any element or compound other than carbon or hydrogen. For example, beneficiating the coal can reduce the amount of mercury in the coal by about at least about 70%, 75%, 80%, 85%, 90%, or 92% or more. In some cases, beneficiating the coal can reduce the water or moisture content of the coal to less than about 5 wt. %, 4 wt. %, 3 wt. %, 2 wt. %, or 1.5 wt. % or lower. In some cases, beneficiating the coal can remove one or more of hydrogen, sulfur, oxygen, arsenic, selenium, cadmium, or volatile matter from the coal. The amount of one or more of these elements in the coal can be reduced by from about 25% to about 90%.

However, in some cases it can be desirable for a desired amount of one or more impurities to remain in the beneficiated coal after being subjected to a beneficiation process. For example, in some embodiments a beneficiation process can remove a desired amount of impurities such that a predetermined amount of cadmium, selenium, or another element can remain in the beneficiated coal after processing. In some cases, the desired amount of impurity that can remain in the coal after beneficiation can be useful in the subsequent formation of advanced carbon materials, and/or can be incorporated into the advanced carbon materials. For example, in some embodiments where the advanced carbon material comprises synthetic graphene, a desired amount of cadmium can remain in the beneficiated coal and can be incorporated into the synthetic graphene to thereby improve the electrical, mechanical, or chemical properties thereof.

In some embodiments, beneficiating the coal can produce various other products that can be captured and used in later processing steps, that can be valuable in and of themselves, or that can be subjected to further processing or use in the method 100. That is, in some embodiments, beneficiating the coal can produce or separate gases or liquids from the raw coal. These gases and/or liquids can be captured or separated during processing. For example, beneficiating the coal at block 120 can produce $H_2$, $CO_2$, CO, $CH_4$, $C_2H_4$, $C_3H_6$, and/or other hydrocarbon gases, which can be captured and subsequently utilized in block 130 or in other process steps. In some cases, beneficiating the coal can result in liquids such as toluene or benzene which can be captured for subsequent use or processing. In some cases, the impurities removed from the coal by the beneficiation process at block 120 can be captured for subsequent use. For example, water removed from the coal by the beneficiation process can be capture and utilized in subsequent process steps. In some embodiments, beneficiating the coal can also produce a solid material known as ash or char. In some cases, this char can be subjected to further processing to form activated ca At block 130 the beneficiated coal, also referred to as upgraded coal, can be processed via the processing facility. In some embodiments, processing the beneficiated coal can include subjecting the upgraded coal to a liquid extraction process, such as a pyrolysis process, a direct liquefaction process, an indirect liquefaction process, or a process including one or more membranes.

In some embodiments, block 130 can comprise pyrolyzing the beneficiated coal via the processing facility. In some embodiments pyrolyzing the beneficiated coal can comprise heating the coal above a desired temperature for a duration. In some cases, the coal can be heated at high pressure and in the presence of a solvent. For example, the upgraded coal can be pyrolyzed in the presence of a $CO_2$ solvent which can be held in a supercritical state. In some cases, the upgraded coal can be pyrolyzed by the MuSCL System developed by TerraPower as described, for example, in U.S. Pat. No. 10,144,874 which is hereby incorporate by reference in its entirety.

In some embodiments, the pyrolysis process can comprise exposing the upgraded coal to electromagnetic radiation at a desired intensity and for a desired duration. For example, block 130 can comprise exposing the upgraded coal to microwave and/or radiofrequency (RF) radiation for a desired duration as part of the pyrolysis process. In some cases, this pyrolysis process can result in the bulk of the upgraded coal remaining below pyrolytic temperatures, while individual particles of coal can be subjected to temperatures greater than about 1200° F. In some cases, this pyrolysis process can also comprise methane activation and/or methylation of at least some of the carbon comprising the upgraded coal. In some embodiments, the upgraded coal can be pyrolyzed by the Wave Liquefaction process developed by H Quest Vanguard, Inc. as described, for example, in U.S. Patent Publication No. 2017/0080399 which is hereby incorporate by reference in its entirety.

In some embodiments, block 130 can comprise subjecting the upgraded coal of block 120 to a liquefaction process. In some embodiments, the liquefaction process can be a direct liquefaction process. In some other embodiments, the liquefaction process can be an indirect liquefaction process.

In some cases where block 130 comprises a direct liquefaction process, the upgraded coal can be heated above a desired temperature for a duration. In some cases, the upgraded coal can be heated in the presence of one or more catalysts and/or at an elevated pressure. In some cases, the upgraded coal can be heated in an atmosphere comprising $H_2$. In some cases, the direct liquefaction process can be a hydrogenation or hydro-cracking process. In some cases, the upgraded coal can be subjected to a direct liquefaction process developed by Axens as described, for example, in U.S. Patent Publication No. 2017/0313886 which is hereby incorporated by reference in its entirety.

In some embodiments, block 130 can comprise an indirect liquefaction process, where the upgraded coal can be converted to a gas or gases, which can then be converted to one or more liquids. For example, an indirect liquefaction process can include heating the upgraded coal to a desired temperature for a desired duration at a desire pressure, such as an elevated pressure. In some cases, this can convert at least some of the upgraded coal to a gas or gases, such as syngas, a mixture of $H_2$ and CO gas. In some cases, these gases, such as syngas, can then be converted to liquids or other materials. For example, the syngas can be converted to ammonia or methanol, which can in turn be subjected to further processing to produce hydrocarbons. In some cases, the gases can be processed to ultimately produce olefins, such as ethylene and propylene. In some cases, the gases can be processed to produce hydrocarbons, such as aromatic hydrocarbons. In some cases, the gases can be processed to produce hydrocarbons such as toluene, benzene, paraxylene, or other hydrocarbons, including polymers and resins. In some cases, the gases can be converted to olefins by a process developed by Honeywell UOP as described, for example, in U.S. Patent Publication No. 2015/0141726 which is hereby incorporated by reference in its entirety. In some cases, the upgraded coal can be subjected to an indirect liquefaction process.

In some embodiments, block 130 can comprise processing the beneficiated coal in the presence of one or more membranes. In some cases, these membranes can serve to physically and/or chemically separate and/or crack the beneficiated coal to produce products therefrom. In some cases, these products can be substantially similar to the products produced by a liquefaction process, but may not use the amount of heat or pressure that a liquefaction process can require. Thus, in some cases, processing beneficiated coal with one or more membranes can produce substantially similar products to a liquefaction process but can require substantially less energy to do so. In some embodiments, the one or more membranes can comprise various pore sizes, chemical properties, physical properties, or electrical properties to isolate desirable compounds and/or produce desirable compounds from the beneficiated coal.

In some embodiments, one or more additives can be added to the beneficiated coal at block 140. In some embodiments, one or more other gases or liquids can be used during the processes of block 140. For example, hydrogen containing gases can be added to or used during a coal liquefaction process. In some cases, natural gases, $CO_2$, or petroleum products can be used as additives during block 130. In some embodiments, the one or more additives can include materials or compounds that are produced during blocks 120 and/or 130, or that can be produced by or captured during previous iterations of process 100.

At block 140, pitch, char, gases, and/or coal liquid are produced via the processing facility. The skilled artisan will appreciated that block 140 can represent the result of blocks 120 and 140, rather than a separate action or process step. While the blocks 110-150 together define the method 100, the method can include additional steps as described herein.

In some embodiments, pitch can be produced via the processing facility at block 140. As used herein, pitch, also known as coal pitch, coal tar, or coal tar pitch, can refer to a mixture of one or more typically viscoelastic polymers as will be well understood by the skilled artisan. In some embodiments, the pitch produced at block 140 can be a direct result of processing the beneficiated coal at step 130. The pitch produced at block 140 can comprise one or more high molecular weight polymers. In some embodiments, the pitch can have a melting point of greater than about 650° F. In some embodiments, the pitch can have a melting point that is high enough that the pitch can be used in a carbon fiber spinning process, for example as described herein, without the need for a plasticizer.

In some embodiments, the pitch can comprise aromatic hydrocarbons, for example polycyclic aromatic hydrocarbons. In some cases, the pitch can comprise at least about 50 wt. % polycyclic aromatic hydrocarbons, at least about 60 wt. %, 70 wt. %, 80 wt. %, 90 wt. %, 95 wt. %, or 99 wt. % or greater of polycyclic aromatic hydrocarbons. In some embodiments, the pitch can be relatively free of impurities, such as water, non-carbon atoms including sulfur or nitrogen, or material such as coal ash or char. In some cases, the pitch can comprise less than about 0.2 wt. % water, less than about 0.1 wt. %, less than about 0.05 wt. %, or less than about 0.01 wt. % water or lower. In some cases, the pitch can comprise less than about 0.1 wt. % ash or other solid material, less than about 0.05 wt. % ash or solid material, or less than about 0.01 wt. % ash or solid material. In some cases, the pitch can have a flash point greater than about 230° F., greater than about 250° F., or greater than about 300° F. In some cases, the pitch can have an API gravity of less than about 4, less than about 3, or less than about 2, or less. In some embodiments, the pitch can have a hydrogen to carbon (H:C) ratio of about 1:1. In some embodiments, the pitch can be an isotropic pitch. In some embodiments, the pitch produced by the method 100 is not coke pitch. That is, in some cases, the pitch produced at block 140 is not produced from coke or a coke based material. In some embodiments, coke is not produced at any point during the method 100.

In some embodiments, char can be produced via the processing facility at block 140. As used herein, char, also known as ash, can refer to any solid material which remains after gases, liquids, and/or pitch have been removed from raw coal. For example, in some embodiments, char can be produced during the beneficiation of raw coal at block 120. In some embodiments, char can be produced by the processing of block 130. In some embodiments, char can be produced as a result of blocks 120 and 130.

In some embodiments, char can comprise a solid high surface area carbonaceous material. In some cases, char can have a relatively low H:C ratio, for example lower than the H:C ratio of pitch produced at block 140. In some cases, char can have an H:C ratio of from about 0.05 to about 0.65. In some cases, char can additionally comprise at least some pitch material, which can be referred to herein as intrinsic binder impregnation. In some cases, any residual pitch or other gaseous or liquid materials can be removed from the char prior to any subsequent processing of the char.

In some embodiments, any char produced at block 140 can be subjected to further processing, for example to produce an advanced carbon material such as activated carbon. In some cases, char can be carbonized or heated, for example in a rotary kiln, as part of this further processing. In some cases the char can then be activated, for example via a physical activation process or a chemical activation process. In some cases, physical activation can comprise heating the char in an atmosphere comprising argon and/or nitrogen, or heating the char in an oxidizing atmosphere. In some cases, chemical activation can comprise impregnating the char with one or more chemicals, such as an acid, a base, or a salt. In some cases, chemical activation can further comprise carbonizing or heating the impregnated char to activate it. In some cases, chemical activation can require lower temperatures and less energy than physical activation. Further, in some cases, chemical byproducts produced by the method 100 can be utilized during the chemical activation process.

In some embodiments, one or more liquids can be produced via the processing facility at block 140. These liquids are referred to collectively as coal liquid extracts herein, and can refer to any material that is extracted or produced from raw coal and is liquid at or near normal temperature and pressure (about 68° F. and 1 atmosphere of pressure). For example, in some embodiments, coal liquid extracts can be produced during the beneficiation of raw coal at block 120. In some embodiments, coal liquid extracts can be produced by the processing of block 130. In some embodiments, coal liquid extracts can be produced as a result of blocks 120 and 130.

In some embodiments, one or more gases can be produced via the processing facility at block 140 and can be captured for later use or reuse. In some embodiments, these gases can be produced during the beneficiation of raw coal at block 120. In some embodiments, gases can be produced by the processing of block 130. In some embodiments, gases can be produced as a result of blocks 120 and 130. In some embodiments, the captured gas or gases can comprise hydrogen and/or carbon. In some cases, the captured gas or gases can comprise sulfur. Such gases can include, for example, $H_2$, $CO_2$, CO, $CH_4$, $C_2H_4$, $C_3H_6$, and/or other hydrocarbon gases. As described herein, in some cases, the captured gases produced by the method 100 can themselves be used as precursors to form advanced carbon materials.

In some embodiments, coal liquid extracts can comprise one or more liquid hydrocarbons. For example, coal liquid extracts can comprise one or more of benzene, toluene, alkanes or paraffins, alkenes, or other saturated or unsaturated hydrocarbons. In some embodiments, coal liquid extracts produced at block 140 can be subjected to further processing, for example to refine or isolate specific liquids, or to convert coal liquid extracts to other liquid compounds. For example, the coal liquid extracts can be subjected to a process to convert one or more of the coal liquid extracts to benzene and/or paraxylenes. In some cases, the coal liquid extracts can be subjected to processing to produce advanced carbon material, such as resins or polymers. In some cases, the coal liquid extracts can be processed to form polyurethane resins, cyanate ester resins, epoxy resins, methacrylate resins, polyester resins, and others.

Pitch, char, gases, and coal liquid extracts are all described as being produced at block 140, however in some embodiments, one or more of these products can be produced at separate times or separate processing steps from any other product. In some embodiments, one or more of pitch, char, and coal liquid extracts can be produced together by a process step and can need to be separated before any further processing of each individual product can occur. For example, pitch and coal liquid extracts can be simultaneously produced as a result of block 130 and can need to be separated from one another, by any process now know or which can be developed in the future, before further processing of either pitch or coal liquid extracts occurs. Accordingly, the method 100 can comprise a further step of separating one or more of the pitch, char, and coal liquid extracts from each other prior to block 150.

At block 150, the pitch produced at block 140 can be treated via the processing facility to produce one or more advanced carbon materials described herein. In some embodiments, the pitch of block 140 is not subjected to further processing or refinement to alter the chemical composition of the pitch before being treated to form an advanced carbon material. However, in some other embodiments, the pitch can be subjected to one or more processes which can alter the chemical composition of the pitch prior to block 150. For example, impurities can be removed from the pitch prior to block 150. In some cases, the pitch can be subjected to one or more processes to produce mesophase pitch or otherwise alter the composition or properties of the pitch In some embodiments, block 150 can comprise processing the pitch to form synthetic graphite. In some cases, the synthetic graphite can be subjected to further processing to form synthetic graphene. For example, in some embodiments block 150 can comprise treating the pitch, for example by exposure to heat, elevated pressure, and/or one or more catalysts to form synthetic graphite. As used herein, the term synthetic graphite is used to refer to any graphite material produced from a precursor material, for example any graphite material that does not occur naturally in the earth. In some embodiments, block 150 can further comprise treating or processing the synthetic graphite to form synthetic graphene. As used herein, synthetic graphene refers to any graphene material produced or derived from synthetically formed graphite. For example, block 150 can comprise subjecting the synthetic graphite to mechanical exfoliation to produce synthetic graphene.

In some embodiments, the method 100 can further comprise capturing at least some of the gases, liquids, or other volatile compounds which can be produced as a result of the method, 100, including blocks 110-150. In some embodiments at least 50%, at least 75%, at least 90%, 95%, or 99% of any gaseous or volatile byproducts of the method 100 can be captured. In some cases, some or all of these captured or retained gaseous or volatile byproducts can then be used in the steps of the method 100. For example, $CO_2$ gas can be produced by one or more of the steps of method 100, which can be captured and subsequently used in any of the steps of method 100. In some cases, the capture and reuse of byproducts can improve the efficiency and/or lower the cost of the method 100.

According to some embodiments, an advanced carbon material can be produced from coal by a method or process including:

providing coal to a processing facility;

beneficiating the coal via the processing facility to remove a desired amount of water, metals, volatile compounds, and other impurities from the coal;

processing at least some of the beneficiated coal via the processing facility;

producing pitch, char, gases, and/or coal liquid extract; and treating one or more of the pitch, char, gases, and/or coal liquid extract via the processing facility to produce one or more advanced carbon materials.

Figure 2:
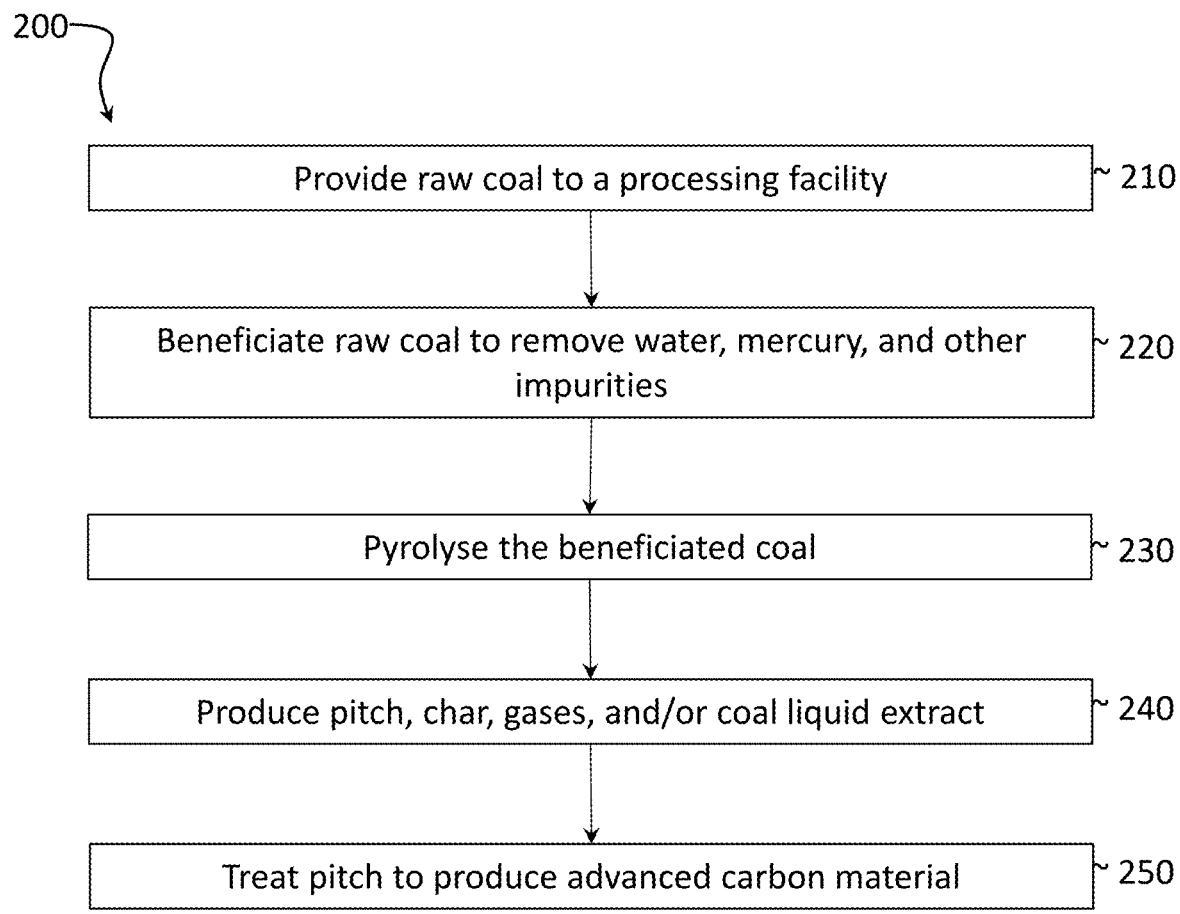
FIG. 2 illustrates a process flow diagram of an example of a method of producing advanced carbon material from coal including a pyrolysis process in accordance with the present disclosure.

According to some embodiments, and as illustrated in FIG. 2, an advanced carbon material can be produced from coal by a method or process 200 including:

providing coal to a processing facility at block 210;

beneficiating the coal via the processing facility at block 220 to remove a desired amount of water, metals, and other impurities from the coal;

pyrolyzing at least some of the beneficiated coal via the processing facility at block 230;

producing pitch, char, gases, and/or coal liquid extract at block 240; and treating at least one of the pitch, char, gases, and coal liquid extract via the processing facility at block 250 to produce the advanced carbon material. Although the method 200 describes a process flow for producing a single type of advanced carbon material via a processing facility, the method 200 can be used to produce more than one type of advanced carbon material via the processing facility. For example, the method 200 can be utilized to produce an amount of a first advanced carbon material and subsequently used to produce an amount of a second, different advanced carbon material. In some cases however, the processing facility can be able to produce two or more different types of advanced carbon materials via parallel processing utilizing the method 200. Further, while producing pitch, char, gases, and/or coal liquid extract is described as a separate block 240, the pitch, char, gases, and/or coal liquid extract can be produced as a result of blocks 220 and/or 230 and may not be a separate process step in and of itself.

Figure 3:
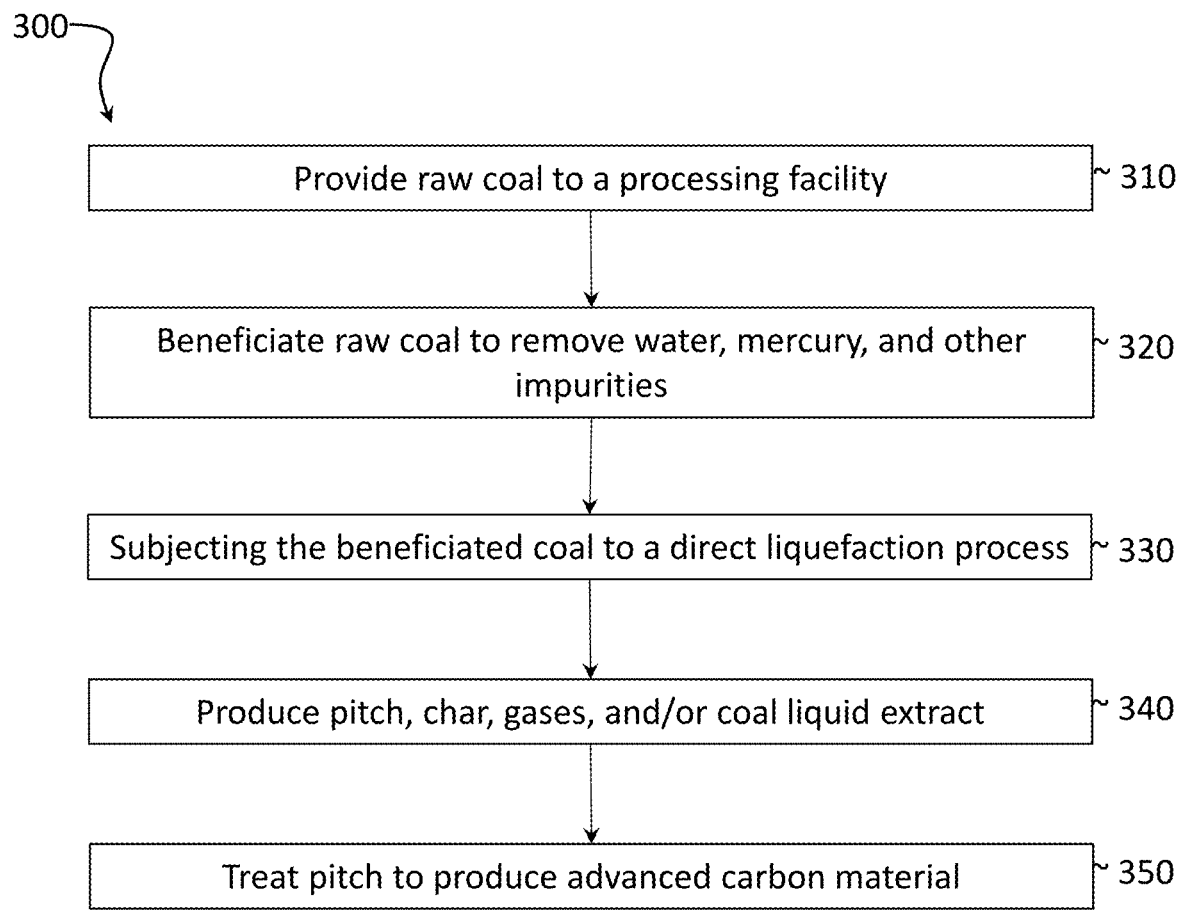
FIG. 3 illustrates a process flow diagram of an example of a method of producing advanced carbon material from coal including a direct liquefaction process in accordance with the present disclosure.

According to some embodiments, and as illustrated in FIG. 3, an advanced carbon material can be produced from coal by a method or process 300 including:

provided coal to a processing facility at block 310;

beneficiating the coal via the processing facility at block 320 to remove a desired amount of water, metals, and other impurities from the coal;

subjecting at least some of the beneficiated coal to a direct liquefaction process via the processing facility at block 330;

producing pitch, char, gases, and/or coal liquid extract at block 340; and treating at least one of the pitch, char, gases, and coal liquid extract via the processing facility at block 350 to produce the advanced carbon material.

Figure 4:
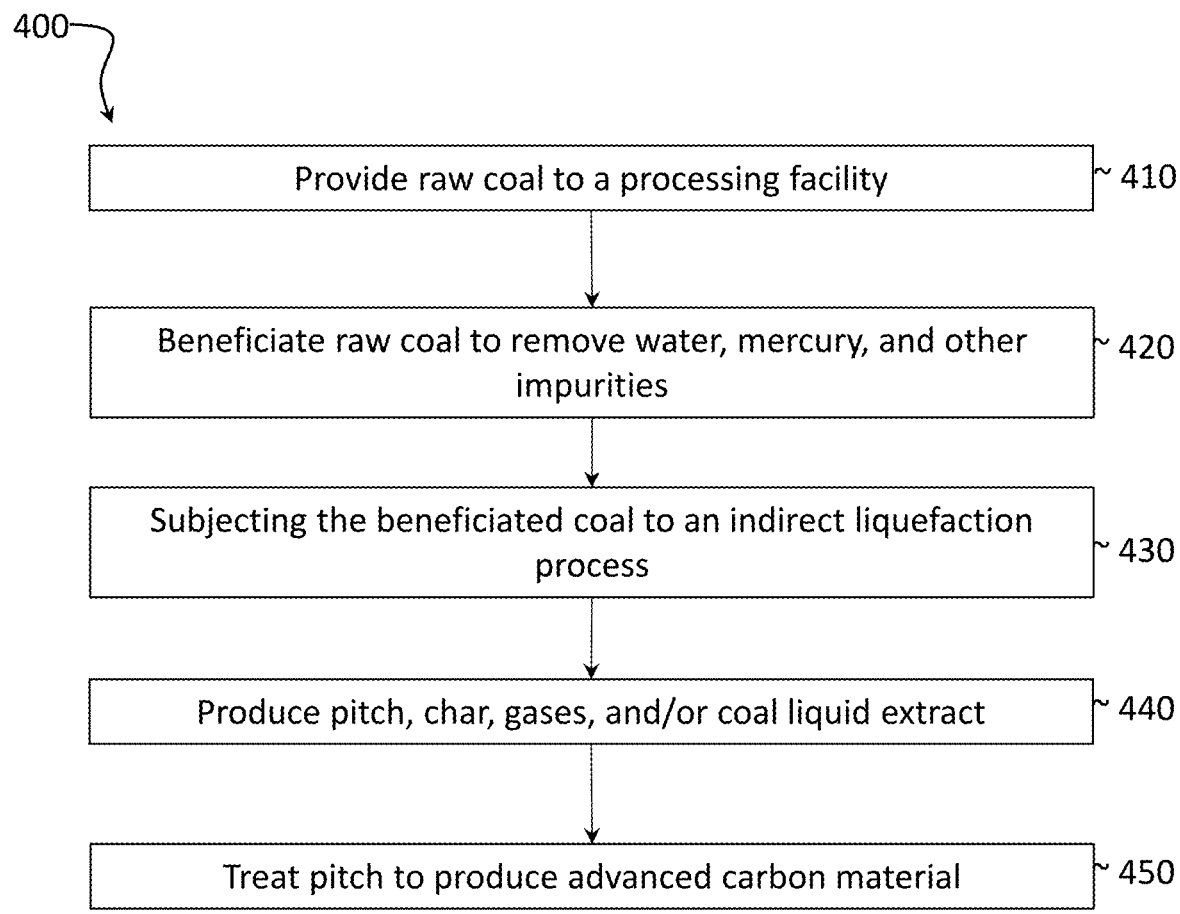
FIG. 4 illustrates a process flow diagram of an example of a method of producing advanced carbon material from coal including an indirect liquefaction process in accordance with the present disclosure.

Although the method 300 describes a process flow for producing a single type of advanced carbon material via a processing facility, the method 300 can be used to produce more than one type of advanced carbon material via the processing facility. For example, the method 300 can be utilized to produce an amount of a first advanced carbon material and subsequently used to produce an amount of a second, different advanced carbon material. In some cases however, the processing facility can be able to produce two or more different types of advanced carbon materials via parallel processing utilizing the method 300. Further, while producing pitch, char, gases, and/or coal liquid extract is described as a separate block 340, the pitch, char, gases, and/or coal liquid extract can be produced as a result of blocks 320 and/or 330 and may not be a separate process step in and of itself. According to some embodiments, and as illustrated in FIG. 4, an advanced carbon material can be produced from coal by a method or process 400 including:

providing coal to a processing facility at block 410;

beneficiating the coal via the processing facility at block 420 to remove a desired amount of water, metals, and other impurities from the coal;

subjecting at least some of the beneficiated coal to an indirect liquefaction process via the processing facility at block 430;

producing pitch, char, gases, and/or coal liquid extract at block 440; and treating at least one of the pitch, char, gases, and coal liquid extract via the processing facility at block 450 to produce the advanced carbon material.

Although the method 400 describes a process flow for producing a single type of advanced carbon material via a processing facility, the method 400 can be used to produce more than one type of advanced carbon material via the processing facility. For example, the method 400 can be utilized to produce an amount of a first advanced carbon material and subsequently used to produce an amount of a second, different advanced carbon material. In some cases however, the processing facility can be able to produce two or more different types of advanced carbon materials via parallel processing utilizing the method 400. Further, while producing pitch, char, gases, and/or coal liquid extract is described as a separate block 440, the pitch, char, gases, and/or coal liquid extract can be produced as a result of blocks 420 and/or 430 and may not be a separate process step in and of itself.

Figure 5:
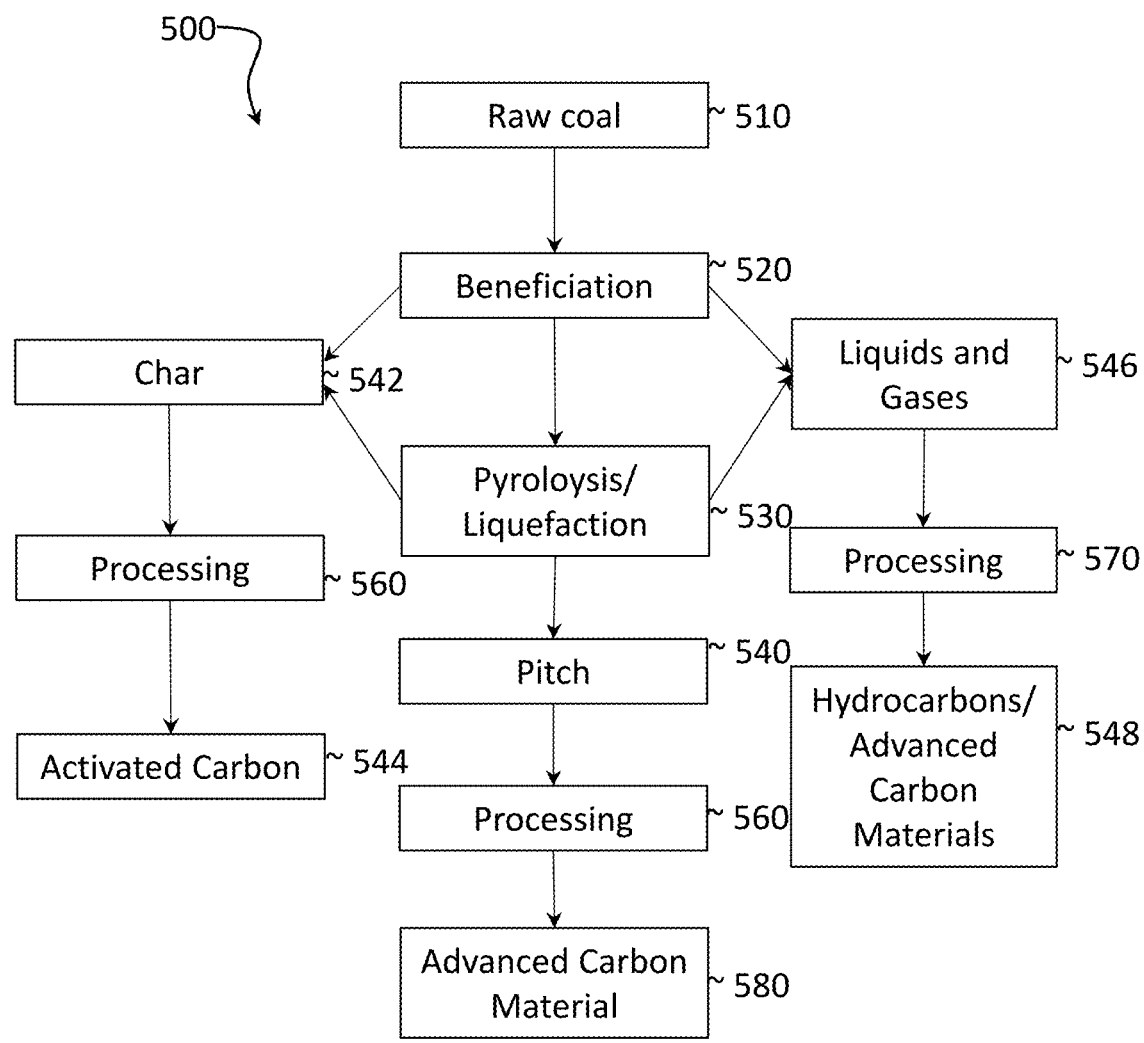
FIG. 5 illustrates a material flow diagram of an example of a method of producing advanced carbon materials from coal in accordance with the present disclosure.

FIG. 5 illustrates a material flow diagram of an example of a method 500 of producing one or more advanced carbon materials from coal in accordance with the present disclosure. At block 510, raw coal is provided to a processing facility, for example by a mining process, such as high wall mining. The raw coal can then be subjected to a beneficiation process to remove a desired amount of water, metals, volatile matter, and other impurities as described herein at block 520. In some cases, the beneficiation process can produce byproducts, such as char (block 542) and gases and/or coal liquid extracts (546), in addition to the upgraded coal. The upgraded coal can be subjected to a pyrolysis, direct liquefaction, or indirect liquefaction process at block 530 and as described herein to produce pitch (block 540). Again, in some cases, the pyrolysis or liquefaction process of block 540 can produce byproducts, such as char (block 542) and coal liquid extracts and gases (block 546). In some cases, the char 542 can be processed or treated at block 560 to produce an advanced carbon material, for example activated carbon (block 544) as described herein. In some cases, the coal liquid extract 546 can be processed or treated at block 570 to produce hydrocarbons, such as benzene and paraxylenes and/or other advanced carbon materials (block 548) as described herein. At block 550, the pitch can be processed or treated to produce one or more advanced carbon materials (block 580), such as carbon fibers or graphene as described herein.

In some embodiments, the method 500 can be entirely carried out at a single processing facility. However, in some other cases, one or more blocks can be carried out at different processing facilities and/or different locations. For example, char 542 or coal liquid extract 546 can be transported to a second location where blocks 560 and 570 can be carried out.

Although the processes described herein relate to the production of advanced carbon materials from coal, in some embodiments these processes can be utilized to produce silicon products, such as silicone resins. For example, in some embodiments, sand or other raw materials comprising silicon can be used in the processes and methods described herein to produce one or more silicone resins.

Figure 6:
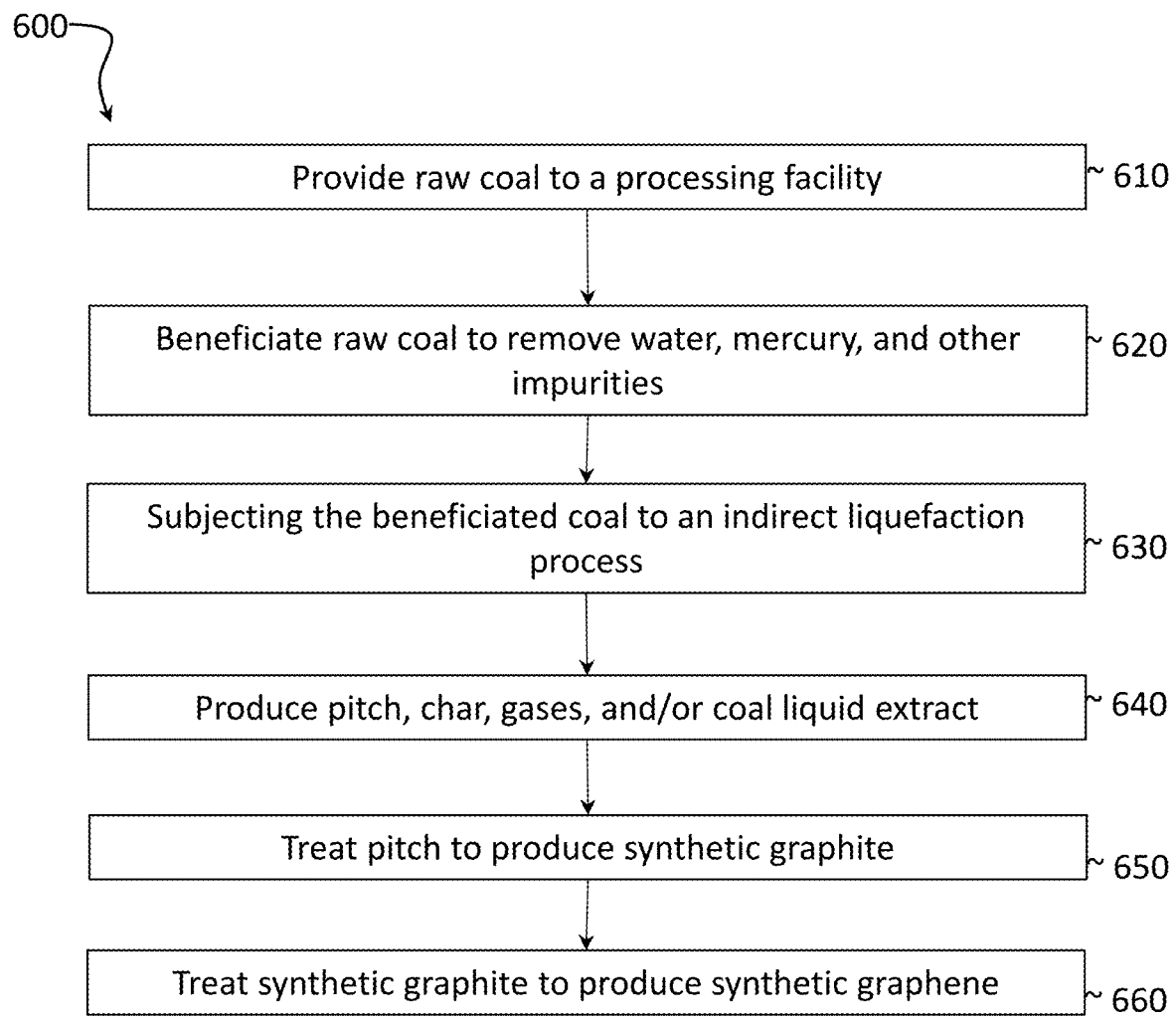
FIG. 6 illustrates a process flow diagram of an example of a method of producing graphene from coal in accordance with the present disclosure.

According to some embodiments, and as illustrated in FIG. 6, synthetic graphene can be produced from coal by a method or process 600 including:

providing coal to a processing facility at block 610;

beneficiating the coal via the processing facility at block 620 to remove a desired amount of water, mercury, cadmium, selenium, other heavy metals, and/or other impurities from the coal;

processing at least some of the beneficiated coal via the processing facility at block 630;

producing pitch, char, gases, and/or coal liquid extract at block 640; and treating at least one of the pitch, char, gases, and coal liquid extract via the processing facility at block 650 to produce synthetic graphite;

treating the synthetic graphite via the processing facility at block 660 to produce the synthetic graphene.

As described herein, a desired amount of one or more impurities can remain in the beneficiated coal at block 620 and can thereby be incorporated into the synthetic graphene produced at block 660 in order to adjust the chemical, electrical, and/or physical properties of the synthetic graphene.

Figure 7:
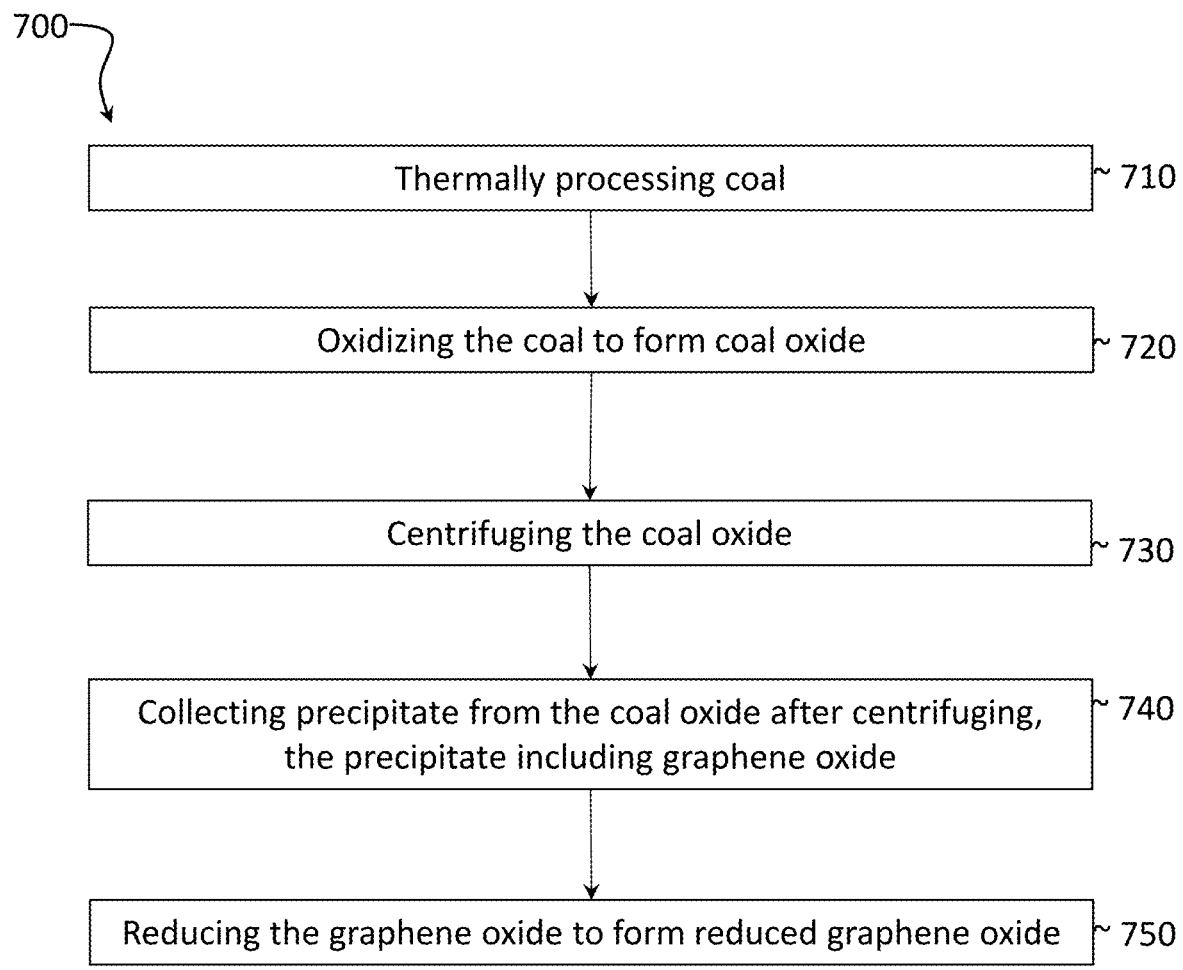
FIG. 7 illustrates a process flow diagram of an example of a method of producing reducing graphene oxide from coal in accordance with the present disclosure.

According to some embodiments, and as illustrated in FIG. 7, graphene or another advanced carbon material can be produced from coal by a method or process 700 including thermally processing coal at block 710 and forming reduced graphene oxide from the coal after the coal has been at least partially cooled from thermal processing. Forming reduced graphene oxide from the coal can include: oxidizing the coal at block 720 to form coal oxide; centrifuging the coal oxide at block 730; collecting precipitate from the coal oxide after centrifuging at block 740, the precipitate including graphene oxide; and reducing the graphene oxide at block 750 to produce reduced graphene oxide. In other embodiments, other activities can be used to form graphene from the thermally-treated coal, such as chemical vapor deposition or formation of carbon dots.

Although the method 700 describes a process flow for producing graphene, the method 700 can be used to produce more than one type of advanced carbon material. For example, the method 700 can be utilized to produce an amount of a first advanced carbon material and subsequently used to produce an amount of a second, different advanced carbon material. In some cases however, two or more different types of advanced carbon materials can be produced via parallel processing utilizing the method 700. Further, various steps of method 700 can each include multiple steps, and various steps of method 700 may not be a separate process steps in and of themselves.

The coal that is thermally processed at block 710 can include raw coal, as described in greater detail above, or coal that is at least partially processed. The raw or at least partially processed coal can include coal crushed to a suitable or predetermined size. Thermally processing the coal can include beneficiating the coal to remove contaminants or impurities, as described above in greater detail. Thermally processing the coal according to this disclosure also can include any of the activities described in U.S. Pat. No. 5,403,365, the disclosures of which are incorporated herein by reference.

In many embodiments, thermally processing coal can include thermally processing coal at a temperature of at least about 300° F. More particularly, in some embodiments, thermally processing coal can include heating the coal to a first temperature not to exceed 350° F., transferring the coal to a mercury removal reactor, heating the coal in the mercury removal reactor to a second temperature of at least 500° F., and contacting the coal with an inert gas to remove at least a portion of mercury present in the coal.

In some embodiments, heating the coal to a first temperature not to exceed 350° F. includes heating the coal to a first temperature not to exceed between about 250° F. and about 350° F., between about 275° F. and about 325° F., between about 285° F. and about 315° F., between about 295° F. and about 305° F., between about 295° F. and about 300° F., between about 300° F. and about 305° F., about 290° F., about 295° F., about 300° F., about 301° F., about 302° F., about 303° F., about 304° F., about 305° F., about 310° F., about 315° F., about 320° F., about 325° F., about 330° F., about 335° F., about 340° F., about 345° F., or about 350° F. When the coal is heated to the first temperature, free water and at least a portion of bound water in the coal is vaporized and removed in a sweep gas. In some embodiments, the coal can be heated in a moisture removal reactor and/or a vibrating fluidized-bed system. Dryer auxiliaries in the moisture removal reactor can include a hot gas generator, a coal feeder, and valves.

After heating the coal to the first temperature, the coal can be transferred to a mercury removal reactor, where the coal can be heated to a second temperature of at least 500° F. In some embodiments, the coal can be heated in the mercury removal reactor to a temperature of between about 400° F. and about 700° F., between about 450° F. and about 650° F., between about 500° F. and about 600° F., between about 525° F. and about 575° F., between about 535° F. and about 570° F., between about 540° F. and about 565° F., between about 545° F. and about 560° F., between about 550° F. and about 555° F., at least about 500° F., at least about 510° F., at least about 520° F., at least about 530° F., at least about 540° F., at least about 545° F., at least about 550° F., at least about 555° F., about 550° F., about 551° F., about 552° F., about 553° F., about 554° F., about 555° F., about 556° F., about 557° F., about 558° F., about 559° F., or about 560° F.

A down-flow reactor can be used to expose the coal to a hot inert gas, which volatizes and removes at least a portion of the mercury and/or at least a portion of one or more dopants. For example, between about 70% and about 80% of the mercury in the coal can be volatized and removed from the coal. In some cases, other dopants or impurities can be removed from the coal, for example, cadmium, selenium, and/or any other element except carbon which may be present in the coal. The coal also can be cooled to a third temperature in the mercury removal reactor, the third temperature being below about 400° F., below about 375° F., below about 350° F., below about 325° F., below about 300° F., below about 275° F., or below about 250° F. Upon cooling to the third temperature, the coal can be reduced in size before forming reduced graphene oxide from the coal.

As noted above, forming reduced graphene oxide from the coal can include: oxidizing the coal at block 720 to form coal oxide; centrifuging the coal oxide at block 730; collecting precipitate from the coal oxide after centrifuging at block 140, the precipitate including graphene oxide; and reducing the graphene oxide at block 150 to produce reduced graphene oxide. At block 720, oxidizing the coal to form a coal oxide can include mixing the coal with at least one of sulfuric acid, nitric acid, or potassium permanganate, or hydrogen peroxide to form the coal oxide. In some embodiments, mixing the coal with at least one of sulfuric acid, nitric acid, potassium permanganate, or hydrogen peroxide to form the coal oxide can include: mixing the coal with sulfuric acid and then mixing nitric acid with the mixture of coal and sulfuric acid.

In some embodiments, mixing the coal with at least one of sulfuric acid, nitric acid, potassium permanganate, or hydrogen peroxide to form the coal oxide can include stirring the mixture of coal, sulfuric acid, and nitric acid for a predetermined period of time. For example, in some embodiments, the mixture of coal, sulfuric acid, and nitric acid can be stirred for at least about 1 hour, at least about 2 hours, at least about 3 hours, at least about 4 hours, at least about 5 hours, between about 1 hours and about 5 hours, between about 2 hours and about 4 hours, between about 2.5 hours and about 3.5 hours, about 1 hour, about 2 hours, about 3 hours, about 4 hours, about 5 hours, less than about 1 hour, less than about 2 hours, less than about 3 hours, less than about 4 hours, or less than about 5 hours.

In some embodiments, mixing the coal with at least one of sulfuric acid, nitric acid, potassium permanganate, or hydrogen peroxide to form the coal oxide can include, after stirring the mixture of coal, sulfuric acid, and nitric acid, mixing potassium permanganate to the mixture of coal, sulfuric acid, and nitric acid and then stirring the mixture of coal, sulfuric acid, nitric acid, and the potassium permanganate for a predetermined period of time. In some embodiments, the mixture of coal, sulfuric acid, nitric acid, and the potassium permanganate can be stirred on a hot plate heated to between about 25° C. and about 45° C., between about 30° C. and about 40° C., between about 33° C. and about 37° C., at least about 25° C., at least about 30° C., at least about 35° C., at least about 40° C., at least about 45° C. about 25° C., about 30° C., about 35° C., about 40° C., or about 45° C. In some embodiments, the mixture of coal, sulfuric acid, nitric acid, and the potassium permanganate can be stirred for at least about 1 hour, at least about 2 hours, at least about 3 hours, at least about 4 hours, at least about 5 hours, at least about 6 hours between about 1 hours and about 6 hours, between about 3 hours and about 5 hours, between about 3.5 hours and about 4.5 hours, about 1 hour, about 2 hours, about 3 hours, about 4 hours, about 5 hours, about 6 hours, less than about 1 hour, less than about 2 hours, less than about 3 hours, less than about 4 hours, less than about 5 hours, or less than about 6 hours.

In some embodiments, mixing the coal with at least one of sulfuric acid, nitric acid, potassium permanganate, or hydrogen peroxide to form the coal oxide can include diluting the mixture of coal, sulfuric acid, nitric acid, and the potassium permanganate with water to form a solution. The mixture of coal, sulfuric acid, nitric acid, and the potassium permanganate with water at a predetermined mixture:water dilution ratio, such as such as about 1:1, about 1:2, about 1:3, about 1:4, about 1:5, about 1:6, about 1:7, or about 1:8.

In some embodiments, mixing the coal with at least one of sulfuric acid, nitric acid, potassium permanganate, or hydrogen peroxide to form the coal oxide can include mixing the solution, as diluted, with hydrogen peroxide. The hydrogen peroxide can include 10% hydrogen peroxide. Upon mixing the hydrogen peroxide with the solution, the solution turns to a yellow or yellow-green color.

In some embodiments, mixing the coal with at least one of sulfuric acid, nitric acid, potassium permanganate, or hydrogen peroxide to form the coal oxide can include performing a first centrifugation of the solution mixed with the hydrogen peroxide. The solution mixed with hydrogen peroxide can be centrifuged for a predetermined period of time, such as at least about 15 minutes, at least about 30 minutes, at least about 45 minutes, at least about 60 minutes, between about 15 minutes and about 45 minutes, about 15 minutes, about 30 minutes, about 45 minutes, or about 60 minutes. The solution mixed with hydrogen peroxide can be centrifuged at a predetermined revolutions per minute (RPM) that can be dependent on the centrifuge machine. In some embodiments, the solution mixed with hydrogen peroxide can be centrifuged at about 500 RPM.

In some embodiments, mixing the coal with at least one of sulfuric acid, nitric acid, potassium permanganate, or hydrogen peroxide to form the coal oxide can include after performing the first centrifugation, separating supernatant of the solution mixed with the hydrogen peroxide from precipitate of the solution mixed with the hydrogen peroxide. The supernatant includes the coal oxide, and the precipitate can be waste. Once the supernatant has been separated from the precipitate, the supernatant can be diluted with water at a predetermined supernatant:water dilution ratio. For example, the supernatant can be diluted with water at a dilution ratio of 1:0.5, 1:1, 1:1.5, 1:2, 0.5:1, 1.5:1, or 2:1.

At block 730, the coal oxide can be centrifuged during a second centrifugation. The coal oxide that is centrifuged can include the dilution of water and coal oxide described above. The coal oxide and water can be centrifuged for a predetermined period of time, such as at least about 10 minutes, at least about 15 minutes, at least about 20 minutes, at least about 25 minutes, at least about 30 minutes, at least about 35 minutes, at least about 40 minutes, between about 10 minutes and about 40 minutes, between about 15 minutes and about 25 minutes, about 15 minutes, about 20 minutes, about 25 minutes, or about 30 minutes. The coal oxide and water can be centrifuged at a predetermined RPM that can be dependent on the centrifuge machine. In some embodiments, the coal oxide and water can be centrifuged at an RPM that is greater than the RPM of centrifuging of the solution mixed with hydrogen peroxide. For example, the coal oxide and water can be centrifuged at greater than 10,000 RPM, such as about 12,800 RPM.

At block 740, graphene oxide can be collected as precipitate after centrifuging the coal oxide and water, and the supernatant of the centrifugation can be waste. In some cases, block 740 can include sonicating the coal oxide while the coal oxide is in water. In some cases, block 740 can include sonicating graphene oxide that has already been collected as a precipitate.

At block 750, the graphene oxide can be reduced to form reduced graphene oxide. Reducing the graphene oxide removes oxygen containing groups from the graphene oxide and at least partially recovers the electrical conductivity of the graphene. In some embodiments, reducing the graphene oxide to form reduced graphene oxide can include at least sonicating the graphene oxide. The interaction between water and a functional group of the graphene oxide promotes exfoliation of the coal oxide layer. The graphene oxide can be sonicated for a predetermined amount of time, such as at least such as at least about 5 minutes, at least about 10 minutes, at least about 15 minutes, at least about 20 minutes, between about 5 minutes and about 15 minutes, about 5 minutes, about 10 minutes, about 15 minutes, or about 20 minutes. After sonication, the graphene oxide and/or reduced graphene oxide can be analyzed to determine the quality of the graphene oxide and/or reduced graphene oxide using a Raman spectroscopy analysis.

In some embodiments, reducing the graphene oxide to form reduced graphene oxide can include hydrothermally treating the graphene oxide in a par reactor after sonicating the graphene oxide. The graphene oxide can be hydrothermally treated in the par reactor for a predetermined amount of time, such as at least about 1 hour, at least about 2 hours, at least about 3 hours, at least about 4 hours, at least about 5 hours, at least about 6 hours between about 1 hours and about 6 hours, between about 3 hours and about 5 hours, between about 3.5 hours and about 4.5 hours, about 1 hour, about 2 hours, about 3 hours, about 4 hours, about 5 hours, about 6 hours, less than about 1 hour, less than about 2 hours, less than about 3 hours, less than about 4 hours, less than about 5 hours, or less than about 6 hours. The graphene oxide can be hydrothermally treated in the par reactor at a predetermined temperature, such as between about 100° C. and about 300° C., between about 130° C. and about 230° C., between about 170° C. and about 190° C., between about 175° C. and about 185° C., at least about 100° C., at least about 140° C., at least about 170° C., at least about 180° C., at least about 190° C., about 170° C., about 175° C., about 180° C., about 185 C, or about 190° C. After the graphene oxide is reduced in the par reactor, the resultant solution is clear with jet black flakes and chunks. The jet black flakes and chunks are reduced graphene oxide, which can be confirmed via Raman spectroscopy.

Figure 8A:
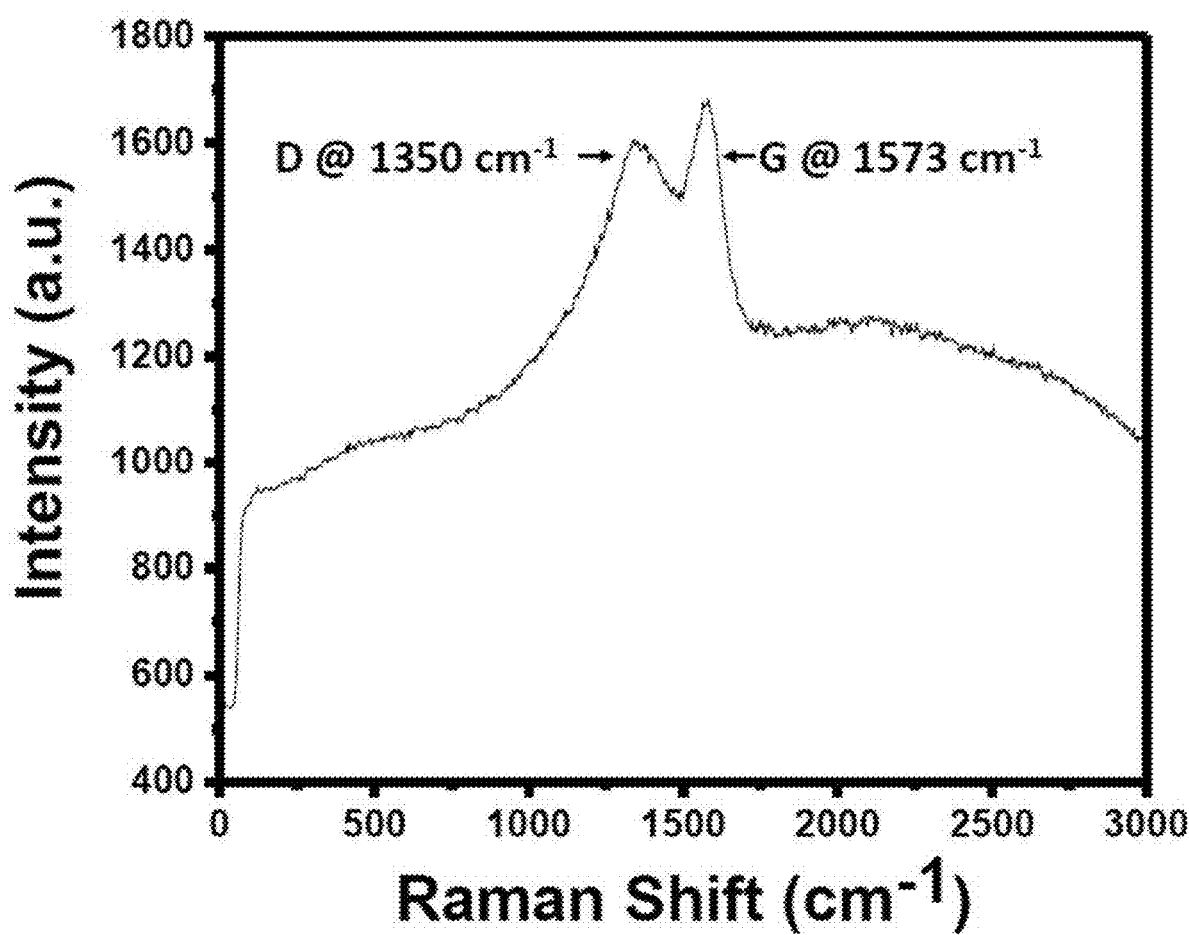
FIG. 8A is a Raman spectroscopy graph of a sample of Monarch seam coal in accordance with the present disclosure.

The steps of one or more embodiments of the method 700 surprisingly produced improved graphene, as demonstrated in the Raman spectroscopy graphs shown in FIGS. 8A-8D. Specifically, FIG. 8A is a Raman spectroscopy graph of a sample of raw (non-thermally-treated) Monarch seam coal. The Monarch seam coal has two characteristic Raman vibrational modes: D-band and G-band. The D-band (1350 $cm^{-1}$) is the defect-induced Raman band. The D-band represents the ring breathing mode of $sp^2$ hybridized carbon. In order to be active, the ring must be adjacent to a graphene edge or a defect. The G-band (1573 $cm^{-1}$) is the first order Raman spectrum, and corresponds to the in-plane vibration of two neighboring carbon atoms on a $sp^2$-hybridized graphene layer. The G peak corresponds to the high-frequency $E_{2g}$ phonon at $\Gamma$-point.

Figure 8B:
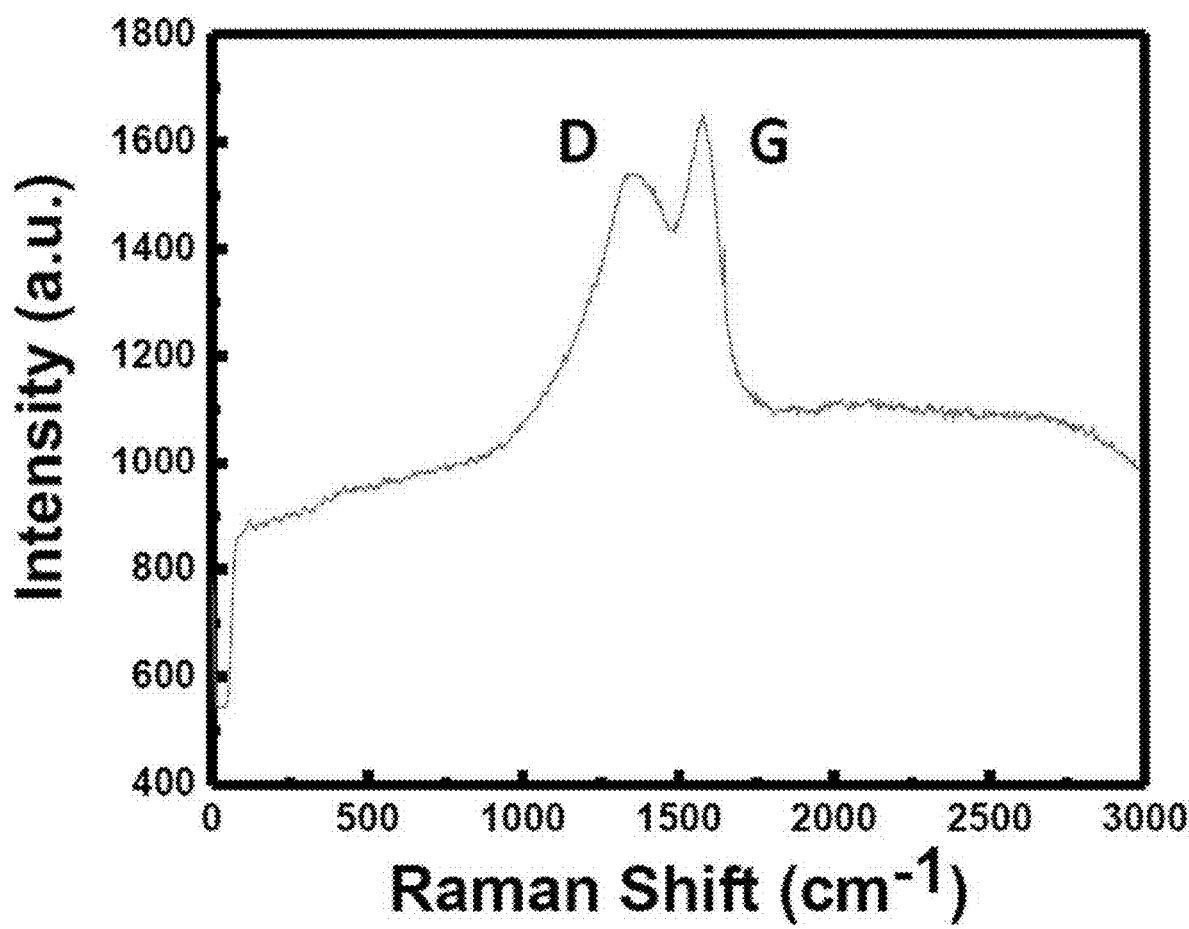
FIG. 8B is a Raman spectroscopy graph of a sample of thermally-treated Monarch seam coal in accordance with the present disclosure.
Figure 8C:
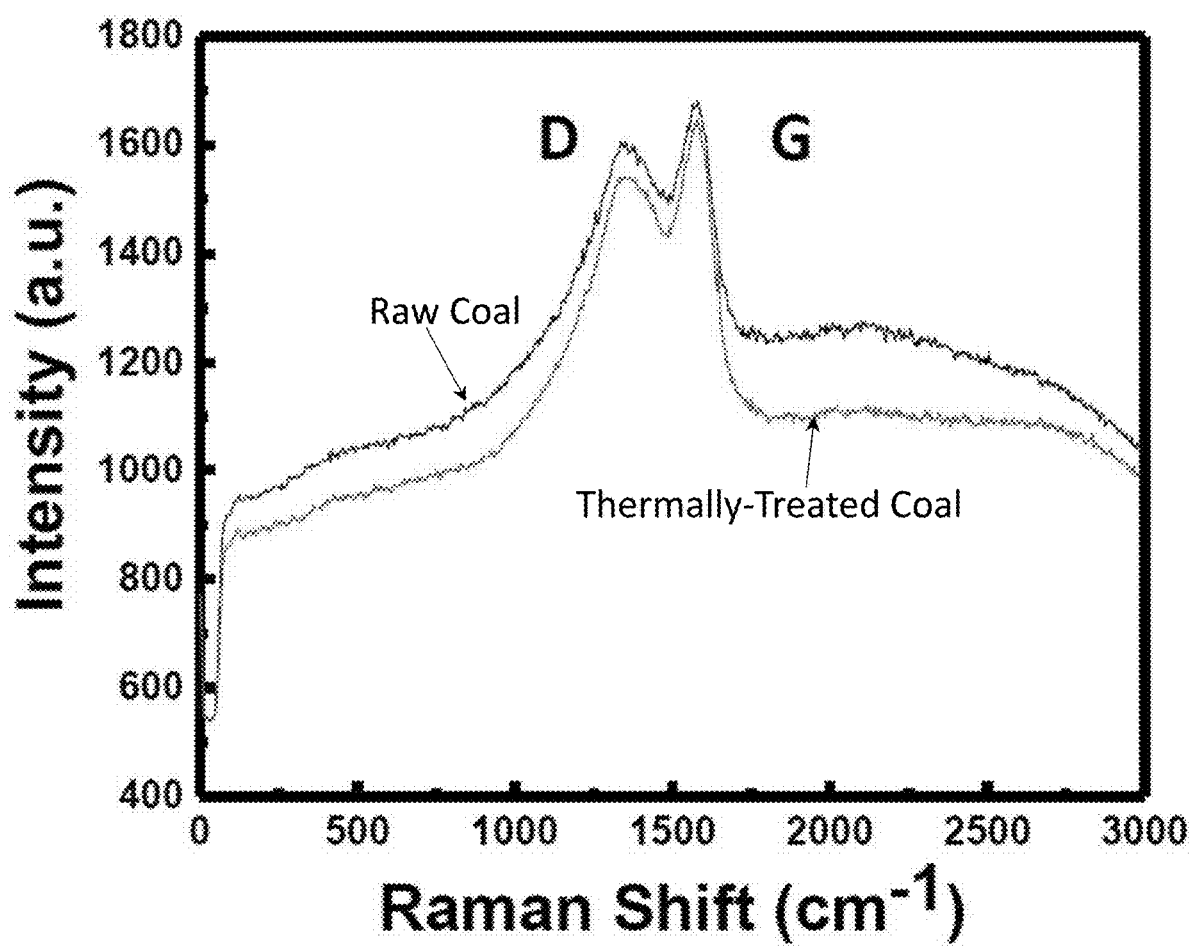
FIG. 8C is a Raman spectroscopy graph comparing the sample of Monarch seam coal of FIG. 8A to the sample of thermally-treated Monarch seam coal of FIG. 8B in accordance with the present disclosure.

FIG. 8B is a Raman spectroscopy graph of a sample of thermally-treated Monarch seam coal. As shown in FIG. 8B, the thermally-treated Monarch seam coal also has two characteristic Raman vibrational modes: D-band and G-band. FIG. 8C is a Raman spectroscopy graph showing a comparison of the sample of Monarch seam coal of FIG. 8A to the sample of thermally-treated Monarch seam coal of FIG. 8B. The comparison indicates that the thermally-treated coal has less defects than the raw Monarch seam coal, as the intensity of the D-band (defect-induced Raman mode) is less. This difference in intensity is shown as $(I_G/I_D)_{Thermally-Treat} > (I_G/I_D)_{Raw}$. The comparison also indicates that graphitization and graphene formation is better in the thermally-treated coal sample, as the G-Band (graphitic-mode) is more sharp and symmetrical in the thermally-treated coal sample than the raw coal sample. Accordingly, thermal-treatment of coal according to this disclosure improves the graphene formation and reduces the defects in the coal.

Figure 8D:
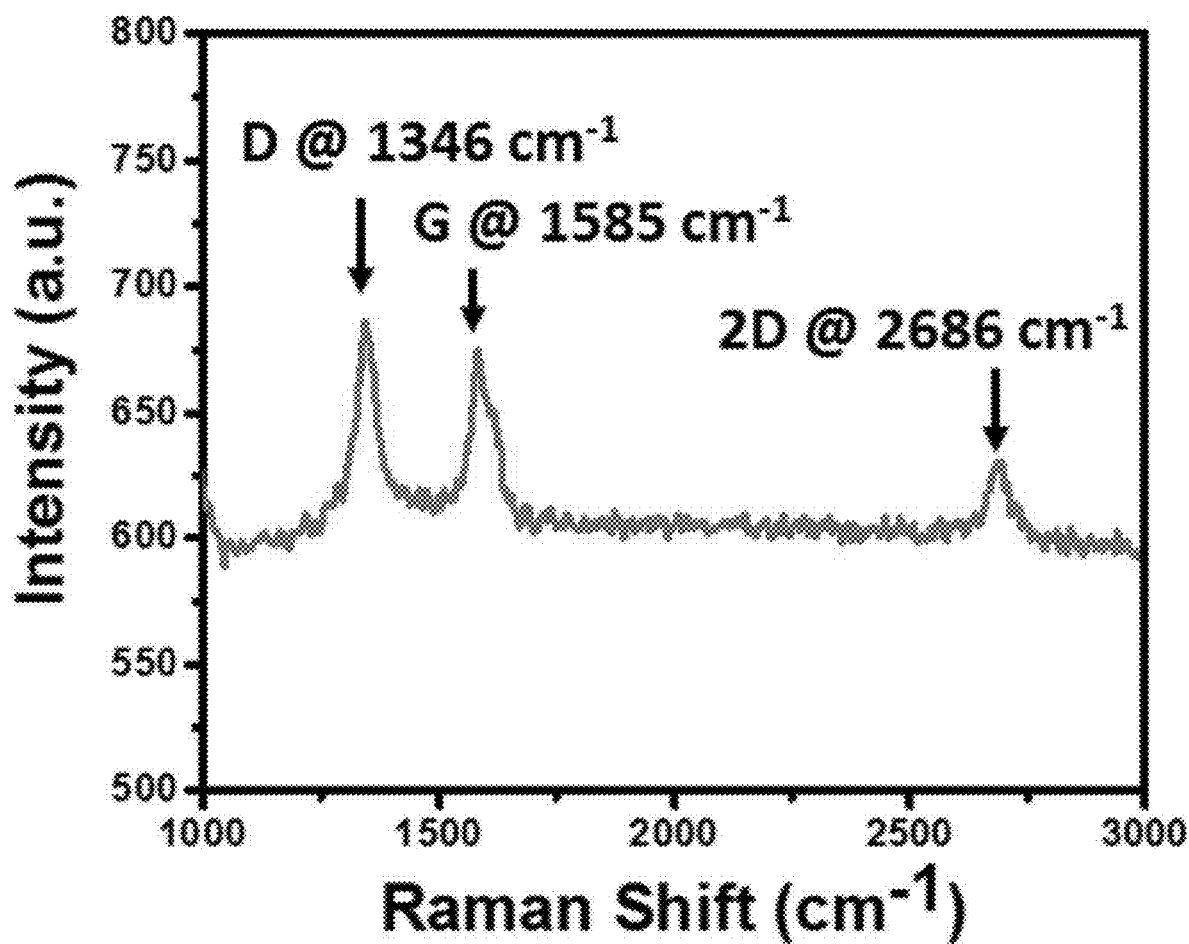
FIG. 8D is a Raman spectroscopy graph of a sample of graphene from thermally-treated Monarch seam coal, in accordance with this disclosure.

FIG. 8D is a Raman spectroscopy graph of a sample of graphene from thermally-treated Monarch seam coal. As can be seen in the figure, the intensity includes three sharp peaks at the D-band, G-band, and 2D-band. The sharpness of these peaks, for example as compared to the relatively broad peaks and overall shape of the graphs of FIGS. 8A-8C indicates the presence of substantially pure graphene. The resultant graph of FIG. 8D is indicative of substantially pure graphene nanoplatelets successfully derived from coal.

The steps of one or more embodiments of the method 700 also surprisingly produced graphene oxide at a high yield rate relative to conventional processes for forming graphene from coal. For example, it was surprisingly observed that the thermally processing coal at a temperature of at least about 300° F. and then forming reduced graphene oxide from the coal yielded reduced graphene oxide at a yield rate of between approximately 10 weight percent and approximately 20 weight percent of the coal. The steps of one or more embodiments of method 700 can yield reduced graphene oxide at a yield rate of at least about 5 weight percent of the coal, at least about 10 weight percent of the coal, at least about 15 weight percent of the coal, at least about 20 weight percent of the coal, at least about 25 weight percent of the coal, at least about 30 weight percent of the coal, at least about 35 weight percent of the coal, at least about 40 weight percent of the coal, at least about 45 weight percent of the coal, at least about 50 weight percent of the coal, between about 2 weight percent and about 50 weight percent of the coal, between about 4 weight percent and about 40 weight percent of the coal, between about 8 weight percent and about 30 weight percent of the coal; between about 10 weight percent and about 20 weight percent of the coal, between about 12 weight percent and about 17 weight percent of the coal, between about 5 weight percent and about 10 weight percent of the coal, between about 10 weight percent and about 15 weight percent of the coal, between about 15 weight percent and about 20 weight percent of the coal, between about 20 weight percent and about 25 weight percent of the coal between about 25 weight percent and about 30 weight percent of the coal, between about 30 weight percent and about 35 weight percent of the coal, between about 35 weight percent and about 40 weight percent of the coal, between about 40 weight percent and about 45 weight percent of the coal, between about 45 weight percent and about 50 weight percent of the coal, about 5 weight percent of the coal, about 10 weight percent of the coal, about 12 weight percent of the coal, about 14 weight percent of the coal, about 16 weight percent of the coal, about 18 weight percent of the coal, about 20 weight percent of the coal, about 22 weight percent of the coal, about 24 weight percent of the coal, about 25 weight percent of the coal, about 30 weight percent of the coal, about 35 weight percent of the coal, about 40 weight percent of the coal, about 45 weight percent of the coal, or about 50 weight percent of the coal.

The steps of one or more embodiments of the method 700 also produced graphene oxide having dopants surprising and useful concentrations. The dopants in the reduced graphene oxide can include one or more of antimony, arsenic, barium, beryllium, boron, bromine, cadmium, chlorine, chromium, cobalt, copper, fluorine, lead, lithium, manganese, mercury, molybdenum, nickel, selenium, silver, strontium, thallium, tin, vanadium, zinc, and/or zirconium. In some cases, the one or more dopants present in the reduced graphene oxide can produce one or more types of defects in the final formed synthetic graphene, such as point defects. In some cases, these defects can enhance or otherwise modify the properties of the resultant graphene, such as the electrical properties. Accordingly, in some cases, a desired amount of one or more dopants in the graphene can result in graphene including a desired amount and/or distribution of defects, such as point defects. The one of more dopants or impurity atoms present in the graphene oxide can be present in concentrations that include up to about 0.1 atomic %, up to about 0.5 atomic %, up to about 1 atomic %, up to about 2 atomic %, up to about 5 atomic %, up to about 10 atomic %, or even up to about 15 atomic % or higher. In some cases the concentration of any of the one or more dopant or impurity atoms in the graphene oxide can include between about 0.1 atomic % and about 15 atomic %, between about 1 atomic % and about 10 atomic %, or between about 2 atomic % and about 5 atomic %, for example.

In some embodiments, the concentrations of one or more dopants in the reduced graphene oxide is controlled during the step(s) of thermally processing the coal, as described in greater detail in relation to block 710 of the method 700. In some embodiments, one or more dopants can be collected in vapor removed during the thermal processing of the coal and at least partially returned at a predetermined concentration to the coal or graphene oxide during one or more steps of the method 700.

Also disclosed herein are various embodiments of a graphene composition including graphene and one or more dopants. The graphene the graphene composition can include one or more of graphene, graphene oxide, and/or reduced graphene oxide in accordance with the method 700. The one or more dopants in the graphene composition can include at least one of antimony, arsenic, barium, beryllium, boron, bromine, cadmium, chlorine, chromium, cobalt, copper, fluorine, lead, lithium, manganese, mercury, molybdenum, nickel, selenium, silver, strontium, thallium, tin, vanadium, zinc, and/or zirconium.

The one of more dopants or impurity atoms present in the graphene can be present in concentrations that include up to about 0.1 atomic %, up to about 0.5 atomic %, up to about 1 atomic %, up to about 2 atomic %, up to about 5 atomic %, up to about 10 atomic %, or even up to about 15 atomic % or higher. In some cases the concentration of any of the one or more dopant or impurity atoms in the finally formed synthetic graphene include between about 0.1 atomic % and about 15 atomic %, between about 1 atomic % and about 10 atomic %, or between about 2 atomic % and about 5 atomic %, for example.

Advanced Carbon Materials

While specific reference has herein been made to the production of graphene, the methods and processes described herein can be used to produce one or more additional advanced carbon materials from coal. As used herein, the term advanced carbon materials can refer to one or more materials comprising carbon. In some embodiments, an advanced carbon material can be an allotrope of carbon and can consist essentially of carbon. In some embodiments, an advanced carbon material can be a resin, polymer, or other hydrocarbon material.

In some cases, an advanced carbon material can comprise primarily carbon atoms. In some embodiments, an advanced carbon material can comprise carbon fibers, carbon foams, activated carbon, and/or pyrolyzed carbon. In some embodiments, an advanced carbon material can comprise one or more allotropes of carbon, for example any allotropes of carbon that are known in the art or that can be developed in the future. In addition to graphene, in some cases, an advanced carbon material can comprise single-walled carbon nanotubes, multi-walled carbon nanotubes, carbon megatubes, carbon nanoribbons, carbon nanobuds, graphite, graphite nano-platelets, quantum dots, and fullerenes, such as buckminsterfullerene and multi-cored fullerenes.

In some cases, an advanced carbon material can comprise elements in addition to carbon and can be, for example, a resin, polymer, or other hydrocarbon material. For example, an advanced carbon material can comprise polyurethane resins, cyanate ester resins, epoxy resins, methacrylate resins, polyester resins, and others. In some cases, an advanced carbon material can comprise thermoset or thermoplastic polymers. In some cases, an advanced carbon material can comprise a polyester, vinyl ester, or nylon polymer.

In some cases, an advanced carbon material can comprise a biologically useful material or biopolymer. That is, in some cases an advanced carbon material can comprise a material including carbon that is used in biological systems or organisms, that is biocompatible, or that can typically be produced by a biological organism. For example, in some embodiments an advanced carbon material can be a protein, amino acid, nucleic acid, collagen, chitosan, sugar, or other biological material. In some cases, an advanced carbon material can comprise a porous material, such as a membrane, for use in a biological and/or chemical process. For example, an advanced carbon material can comprise perforated graphene.

In some embodiments where the advanced carbon material can comprise carbon fibers, the carbon fibers can have different or improved physical properties as compared to carbon fibers formed by conventional processes, for example by spinning polyacrylonitrile (PAN). In some cases, carbon fibers produced by the processes described herein can have a higher degree of molecular orientation along the fiber axis than carbon fibers produced from PAN. In some cases, carbon fibers produced by the processes described herein can have a higher elastic modulus than carbon fibers produced from PAN. In some cases, carbon fibers produced by the processes described herein can have a higher thermal and electrical conductivity than carbon fibers produced from PAN. However, in some embodiments, an advanced carbon material can comprise PAN, and thus carbon fibers can be produced from PAN that is formed from coal according to the processes described herein.

Applications

The advanced carbon material or materials produced via the methods and processes described herein can be used in a wide variety of applications. In some cases, the advanced carbon materials produced via the processing facility described herein can be subjected to further processing to produce objects, devices, and other products from the advanced carbon materials. In other embodiments, the advanced carbon materials can be distributed to other production facilities for use. Importantly, in some embodiments, the processes described herein can produce two or more types of advanced carbon materials which can be combined at the processing facility into further products.

In some cases, an advanced carbon material, such as graphene, can be functionalized and tuned as desired. In some cases, any of the advanced carbon materials or forms of graphene described herein can be used to adsorb desired elements or compounds or to form functionalized products. For example, in some cases an advanced carbon material produced according to the methods described herein can be functionalized to adsorb one or more predetermined materials, elements, and/or substances from water, the atmosphere, or other mediums as desired. In some cases, advanced carbon material produced according to the methods described herein can adsorb one or more types of rare earth elements produced by coal processing plants, such as the processing facilities described herein. In some cases, advanced carbon material produced according to the methods described herein can adsorb one or more valuable predetermined elements or compounds from sea water. In some cases, advanced carbon material produced according to the methods described herein can adsorb $CO_2$ from the ambient atmosphere.

In some cases, graphene formed according to the methods described herein can be used as a support or substrate for one or more elements or compounds. In some cases, these elements or compounds can be utilized to perform desired applications or to have predetermined electrical, chemical, and/or physical properties. For example, in some cases graphene formed according to the methods described herein can be arranged in layers to serve as a support, scaffold, or substrate for one or more enzymes that can serve any number of desired functions. In some cases, enzymes supported by a graphene support structure can adsorb $CO_2$, for example from the ambient environment, to be converted into a secondary product, such as methane.

In some cases, and as described herein, a first amount of pitch can be treated to produce a first advanced carbon material, and a second amount of pitch can be treated to produce a second, different advanced carbon material. In some cases, the first and second advanced carbon materials can be combined to form a new material and/or produce. For example, the first advanced carbon material can comprise carbon fibers and the second advanced carbon can comprise a polymer or resin. The first and second advanced carbon materials can then be combined via the processing facility to produce carbon fiber reinforced polymer by any process known in the art or that can be developed in the future. In some cases, the carbon fiber reinforced polymer can be formed into a desired structure, for example a part or product as specified by a customer. In some embodiments, an advanced carbon material can be produced via the processes described herein and can be combined with one or more other materials via the processing facility to produce a composite material having a desired form. For example, the advanced carbon material can comprise carbon nanotubes. These carbon nanotubes can then be metalized via the processing facility to produce a carbon nanotube metal matrix composite. In some cases, the carbon nanotube metal matrix composite can comprise a bulk material, however in some other cases the carbon nanotube metal matrix composite can be formed in a desired shape. In some cases, a carbon nanotube metal matrix composite can be formed by any processes known in the art or that can be developed in the future, such as via powder metallurgy processes, electrochemical processes, melt processes, and others.

In some embodiments where an advanced carbon material can comprise a resin, the resin can be subjected to further processing via the processing facility to produce a polymer part or product. In some cases, the resin can be used in a three dimensional printing process to form polymer structures such as meshes, hollow objects, solid objects, or other products. In some embodiments, a resin produced by the processes described herein can be used in a continuous liquid interface production (CLIP) process as developed by Carbon3D, Inc., to produce a wide variety of polymer objects via the processing facility. Carbon3D, Inc. uses a number of different resins to provide end products with selectable properties via the CLIP process. In some embodiments, the methods and processes described herein can be used to produce any of the resins used in the CLIP process, for example, polyurethane resins, ester resins, epoxy resins, and others. Accordingly, the processing facility can comprise one or more CLIP printers, such as the M2 Printer developed by Carbon3D, Inc., which can print polymer parts derived directly from coal as described herein. For example, in some embodiments, advanced carbon materials produced from coal by the processes described herein can be used in the CLIP process via the processing facility to print dental products which are customized to an individual patient's anatomy. While custom dental products are provided as an example, almost any form of three-dimensional object can be produced via the processes described herein.

For example, in some embodiments where an advanced carbon material comprises one or more resins for use in 3D printing, such resins can be used to 3D print products specific to the needs of each customer. For example, such 3D printed products can have dimensions corresponding to the custom measurements of each customer. In some examples, products 3D printed using resins produced via the processes described herein can include custom helmets, pads, or other protective clothing for use in sporting activities and/or combat. In some embodiments, one or more body parts of a user or customer can be scanned and the dimensions thereof can be incorporated into the custom design of the 3D printed product. In some cases, custom 3D printed products using resins produced via the processes described herein can include custom fitted horse shoes and/or saddles.

In some embodiments, the advanced carbon material resins used in a 3D printing process can be modified on site by a user in order to achieve the desired chemical or mechanical properties of the final 3D printed product. For example, a first resin produced from coal by the processes described herein can have a first physical property in a final cured state, such as a first young's modulus. Where a user desires to adjust this property, they can be direct to add a predetermined amount of a second resin or other advanced carbon material produced from coal to the first resin, where the second resin and amount thereof can be selected based on the nature of the adjustment to the first physical property of the first resin produced from coal. For example, where a user desires a higher young's modulus, they can be directed to add a predetermined amount of a second resin produced from coal in order to raise the young's modulus of the first resin. In some cases, this addition can be carried out automatically based on the desired cured material properties of the 3D printed object.

In some embodiments, the material properties of a 3D printed objected can be varied throughout the volume of the object by utilizing two or more resins produced form coal according to the processes described herein that are UV activatable, where each of the two or more resins has different material properties when cured and each is activated by a different wavelength of UV light. For example, in some embodiments a first resin produced from coal having a first material property, such as a first stiffness, can be activated by a first wavelength of UV light. A second resin produced from coal having a second, different material property, such as a second stiffness, can be activated by a second, different wavelength of UV light. The resins can be activated by UV light to form the product as it is being 3D printed, and the wavelength of the UV light can be adjusted to vary the material properties of the product as it is being printed. For example, UV light having a wavelength corresponding to the activation wavelength of the first resign can be used for those parts of the product where the material properties of the first resin are desired. The wavelength can then be varied or changed to the activation wavelength of the second resin so that the material properties of the printed object vary from the properties of the first resin to the properties of the second.

In some embodiments, graphene or other advanced carbon materials can be used in the production of graphene or functionalized graphene ink. Graphene inks can be generated from graphene in accordance with the present disclosure and printed onto a source or poured into channel to produce a graphene-based array.

In some embodiments, a first advanced carbon material produced by the processes described herein can be used in a subsequent such process to produce a second, different advanced carbon material. For example, the first advanced carbon material can comprise molecular graphene membranes. The molecular graphene membranes can then be used in the processes described herein to chemically separate products of pyrolysis or liquefaction processes to produce resins. In some cases, this form of chemical separation via graphene membranes can be more thermally efficient than other separation processes that are typically employed. These resins in turn can be used in the CLIP process, for example to print a mesh.

In some embodiments where an advanced carbon material comprises graphene, the graphene can be subjected to further treatment via the processing facility to form, for example, a graphene sensor. In some embodiments, a graphene sensor can include graphene ink. For example, a graphene sensor can include undoped graphene ink as the circuit to an area or point that contains doped graphene. In such an embodiment, the doped graphene area or point can detect, and the undoped graphene ink can carry a signal to a computing device or user interface. In some embodiments, a graphene sensor can include a flake-based graphene sensor, such as a flake-based graphene biosensor. In such embodiments, some graphene flakes can be doped, and some graphene flakes and/or graphene ink acting as a circuit will not be doped. These graphene sensors can be used as disposable chips for detecting diseases via a handheld device. The graphene sensor can be able to immediately detect diseases, such as Lyme disease or the zika virus from a patient's blood, urine, saliva, or other bodily fluids or biological material, thereby eliminating any need to store blood samples for transportation to a lab. Further, the processes described herein can also be used to print the body of the hand-held device, and/or a consumable or attachment, such as a microfluidic chamber, for example via the CLIP process.

In some embodiments, advanced carbon materials produced by the processes described herein can be used in a wide variety of other applications. For example, the advanced carbon material can comprise a carbon foam which can be used as an electrode in a lithium ion battery. More specifically, graphene or reduced graphene oxide produced by the processes described herein can be used in an electrode in a battery. The graphene or reduced graphene oxide produced by the processes described herein used in an electrode in a battery can include one or more of the dopants described herein at any of the amounts described herein. In some cases, the advanced carbon material can comprise activated carbon that can be used in an atmospheric $CO_2$ recapture process. In some cases, the atmospheric $CO_2$ recapture process can be carried out via the processing facility and captured $CO_2$ can be used in the processes described herein.

In some embodiments, advanced carbon materials, such as graphene, formed according to the processes described herein can be used to produce solar panels. In some cases these solar panels can have greater efficiencies than other conventionally produced solar panels. In some embodiments, advanced carbon materials formed according to the processes described herein can be used as precursors in electrospinning processes. For example, advanced carbon materials can be used to electrospin scaffolds or other structures having micron level resolution. In some cases the advanced carbon materials used in electrospinning can be biomaterials produced from coal according to the processes described herein. In some embodiments advanced carbon materials can be used to produce gels, for example medical grade gels such as hydrogels or silicone gels.

In some embodiments, one or more advanced carbon materials produced from coal according to the processes described herein can be used as automotive grade materials in the production of cars, trucks, or other automobiles. For example, carbon fibers, resins, and/or CFRPs can be used as automotive frames, structural components, body panels, engine blocks, and/or other components. In some cases, the components can be 3D printed and can be custom designed according to a user's preferences.

In some embodiments, one or more advanced carbon materials produced from coal according to the processes described herein can be used to form products for use in chemical or biological processes, such chromatography columns, membranes, and filters. In some cases, chromatography columns, membranes, and/or filters can be 3D printed from one or more advanced carbon materials produced from coal according to the processes described herein. In some cases, the chromatography columns, membranes, and/or filters can be used to isolate or remove antibodies, bacteria, parasites, and/or heavy metals from various solutions.

In some embodiments, reinforced graphene can be produced in accordance with the disclosures of the present application. The reinforced graphene includes graphene and nanotubes. Advantageously, graphene having one or more dopants described herein can chemically bond with nanotubes having another dopant. This chemical bond can form between the carbon nanotube and the graphene sheet, and can allow the repetitive layers of graphene sheets to form a graphene filter. Graphene filters in accordance with the present disclosure also can be formed using chemical linkers. For example, different dopant metals on each end of chemical linkers allow the chemical linkers to be directional and control the space between the graphene sheets, the graphene sheets being pre-doped with reactive dopants that are different to the chemical linkers.

In some embodiments, one or more advanced carbon materials produced from coal according to the processes described herein can be used to form circuit boards. For example, a carbon foam produced from coal as described herein can be 3D printed to form a circuit board. In some cases a carbon foam circuit board can have superior electrical and thermal properties to typical printed circuit boards. In some embodiments, one or more advanced carbon materials produced from coal according to the processes described herein can be synthetic graphene and can be used in a variety of electronic applications, for example in forming quantum dots and in computer chips. In some cases, graphene can be used to produce biosensors that can be capable of isolating and/or identifying any number of biologically active molecules or substances, such as disease biomarkers or viruses.

In some embodiments, one or more advanced carbon materials produced from coal according to the processes described herein can include composite materials, such as metals or concrete including carbon fibers, graphene, or other advanced carbon materials. In some examples, metal including one or more advanced carbon materials such as graphene, carbon fibers, or carbon nanotubes can be 3D printed. In some examples, carbon fiber or CFRPs produced from coal as described herein can be used as rebar in concrete or can be used as other construction or building materials.

Unless otherwise indicated, all numbers or expressions, such as those expressing dimensions, physical characteristics, etc., used in the specification (other than the claims) are understood as modified in all instances by the term "approximately." At the very least, and not as an attempt to limit the application of the doctrine of equivalents to the claims, each numerical parameter recited in the specification or claims which is modified by the term "approximately" should at least be construed in light of the number of recited significant digits and by applying ordinary rounding techniques.

In addition, all ranges disclosed herein are to be understood to encompass and provide support for claims that recite any and all subranges or any and all individual values subsumed therein. For example, a stated range of 1 to 10 should be considered to include and provide support for claims that recite any and all subranges or individual values that are between and/or inclusive of the minimum value of 1 and the maximum value of 10; that is, all subranges beginning with a minimum value of 1 or more and ending with a maximum value of 10 or less (e.g., 5.5 to 10, 2.34 to 3.56, and so forth) or any values from 1 to 10 (e.g., 3, 5.8, 9.9994, and so forth).

We claim:

1. A method of producing reduced graphene oxide, comprising:
   thermally processing an amount of coal to achieve a predetermined concentration of an one or more impurity atoms in the amount of coal;
   oxidizing at least some of the amount of coal to form a coal oxide including a predetermined concentration of the one or more impurity atoms;
   processing the coal oxide to form reduced graphene oxide including a predetermined concentration between about 0.1 atomic % and about 10 atomic % of the one or more impurity atoms.

2. The method of claim 1, wherein the one or more impurity atoms occur naturally in the amount of coal.

3. The method of claim 1, wherein the one or more impurity atoms comprise one or more of cadmium, selenium, boron, nitrogen, or silicon.

4. The method of claim 1, wherein the impurity atoms comprise one or more of boron, nitrogen, or silicon.

5. The method of claim 1, wherein thermally processing the amount of coal comprises heating the amount of coal to a temperature of at least about 300° F.

6. The method of claim 1, wherein thermally processing the amount of coal comprises:
heating the amount of coal to a first temperature of less than 350° F.;
transferring the coal to a mercury removal reactor; and
heating the amount of coal in the mercury removal reactor to a second temperature of at least 500° F.; and
contacting the amount of coal with an inert gas to remove at least a portion of mercury present in the coal.

7. The method of claim 1, wherein processing the coal oxide to form reduced graphene oxide comprises:
centrifuging the coal oxide;
collecting a precipitate from the coal oxide after centrifuging, the precipitate comprising graphene oxide; and
reducing the graphene oxide to form reduced graphene oxide.

8. The method of claim 7, further comprising diluting the coal oxide with water before centrifuging the coal oxide.

9. The method of claim 7, wherein reducing the graphene oxide to form reduced graphene oxide comprises:
sonicating the graphene oxide; and
hydrothermally treating the graphene oxide in a par reactor after sonicating the graphene oxide.

10. The method of claim 1, wherein processing the coal oxide to form reduced graphene oxide comprises forming the reduced graphene oxide from the coal oxide at a reduced graphene oxide yield rate of between about 10 weight percent and about 20 weight percent of the amount of coal.

11. The method of claim 1, wherein oxidizing at least some of the amount of coal comprises mixing at least some of the amount of coal with at least one of sulfuric acid, nitric acid, potassium permanganate, or hydrogen peroxide.

12. The method of claim 11, wherein mixing at least some of the amount of coal with at least one of sulfuric acid, nitric acid, potassium permanganate, or hydrogen peroxide comprises:
mixing the coal with at least one of sulfuric acid or nitric acid;
stirring the coal mixed with at least one of sulfuric acid or nitric acid;
mixing potassium permanganate with the coal mixed with at least one of sulfuric acid or nitric acid;
stirring the coal mixed with the potassium permanganate and at least one of sulfuric acid or nitric acid;
diluting, with water, the coal mixed with potassium permanganate and at least one of sulfuric acid or nitric acid to form a solution;
mixing the solution with hydrogen peroxide;
performing a first centrifuging of the solution mixed with hydrogen peroxide; and
separating a supernatant of the solution mixed with hydrogen peroxide from a precipitate of the solution mixed with the hydrogen peroxide, the supernatant comprising the coal oxide.

\* \* \* \* \*